United States Patent
Shaikh et al.

(10) Patent No.: US 10,214,466 B2
(45) Date of Patent: Feb. 26, 2019

(54) SYSTEMS AND METHODS FOR PRODUCING PROPYLENE

(71) Applicant: Saudi Arabian Oil Company, Dhahran (SA)

(72) Inventors: Sohel Shaikh, Dhahran (SA); Aqil Jamal, Dhahran (SA); Zhonglin Zhang, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/043,924

(22) Filed: Jul. 24, 2018

(65) Prior Publication Data

US 2018/0327338 A1 Nov. 15, 2018

Related U.S. Application Data

(62) Division of application No. 15/190,964, filed on Jun. 23, 2016, now Pat. No. 10,059,645.

(Continued)

(51) Int. Cl.
| | |
|---|---|
| *C07C 6/04* | (2006.01) |
| *C07C 4/02* | (2006.01) |
| *C07C 4/06* | (2006.01) |
| *B01J 23/30* | (2006.01) |
| *B01J 35/02* | (2006.01) |

(Continued)

(52) U.S. Cl.
CPC ............. *C07C 6/04* (2013.01); *B01J 23/30* (2013.01); *B01J 29/035* (2013.01); *B01J 29/0341* (2013.01); *B01J 29/40* (2013.01); *B01J 35/002* (2013.01); *B01J 35/0006* (2013.01); *B01J 35/023* (2013.01); *B01J 37/0201* (2013.01); *C07C 4/06* (2013.01); *B01J 29/005* (2013.01); *C07C 2521/08* (2013.01);

(Continued)

(58) Field of Classification Search
CPC .................................... C07C 6/04; C07C 4/02
USPC ................................ 585/324, 650, 643, 645
See application file for complete search history.

(56) References Cited

U.S. PATENT DOCUMENTS

| | | |
|---|---|---|
| 3,546,313 A | 12/1970 | Banks |
| 3,586,731 A | 6/1971 | Heckelsberg |

(Continued)

FOREIGN PATENT DOCUMENTS

| | | |
|---|---|---|
| CN | 101531558 A | 9/2009 |
| CN | 102325742 A | 1/2012 |

(Continued)

OTHER PUBLICATIONS

Arudra et al., "Silicalite-1 as Efficient Catalyst for Production of Propene from 1-Butene", ACS Catalysis, 2014, 4205-4212, 4, American Chemical Society.

(Continued)

*Primary Examiner* — Thuan D Dang
(74) *Attorney, Agent, or Firm* — Dinsmore & Shol LLP

(57) ABSTRACT

According to one embodiment described in this disclosure, a process for producing propylene may comprise at least partially metathesizing a first stream comprising at least about 10 wt. % butene to form a metathesis-reaction product, at least partially cracking the metathesis-reaction product to form a cracking-reaction product comprising propylene, and at least partially separating propylene from the cracking-reaction product to form a product stream comprising at least about 80 wt. % propylene.

15 Claims, 9 Drawing Sheets

Related U.S. Application Data

(60) Provisional application No. 62/188,052, filed on Jul. 2, 2015.

(51) Int. Cl.

| | |
|---|---|
| *B01J 35/00* | (2006.01) |
| *B01J 29/03* | (2006.01) |
| *B01J 29/035* | (2006.01) |
| *B01J 29/40* | (2006.01) |
| *B01J 37/02* | (2006.01) |
| *B01J 29/00* | (2006.01) |

(52) U.S. Cl.
CPC ...... C07C 2523/30 (2013.01); C07C 2529/40 (2013.01); Y02P 20/52 (2015.11)

(56) References Cited

U.S. PATENT DOCUMENTS

| | | |
|---|---|---|
| 3,702,886 A | 11/1972 | Argauer et al. |
| 4,024,201 A | 5/1977 | Takahashi |
| 4,071,471 A | 1/1978 | Banks et al. |
| 4,575,575 A | 3/1986 | Drake et al. |
| 4,609,769 A | 9/1986 | Kukes et al. |
| 5,026,935 A | 6/1991 | Leyshon et al. |
| 5,026,936 A | 6/1991 | Leyshon et al. |
| 6,207,115 B1 | 3/2001 | Chodorge et al. |
| 6,538,168 B1 | 3/2003 | Schwab et al. |
| 6,586,649 B1 | 7/2003 | Botha et al. |
| 6,646,172 B1 | 11/2003 | Schwab et al. |
| 6,777,582 B2 | 8/2004 | Gartside et al. |
| 6,977,321 B1 | 12/2005 | Dath et al. |
| 7,214,841 B2 | 5/2007 | Gartside et al. |
| 7,754,647 B2 | 7/2010 | Schubert et al. |
| 7,754,934 B2 | 7/2010 | Tsunoda et al. |
| 8,299,313 B2 | 10/2012 | Takai et al. |
| 8,324,440 B2 | 12/2012 | Popp et al. |
| 8,440,874 B2 | 5/2013 | Ramachandran et al. |
| 8,586,813 B2 | 11/2013 | Ramachandran et al. |
| 8,722,568 B2 | 5/2014 | Popp et al. |
| 9,834,497 B2 | 12/2017 | Shaikh et al. |
| 9,884,794 B2 | 2/2018 | Al-Khattaf et al. |
| 2004/0254411 A1 | 12/2004 | Steinbrenner et al. |
| 2005/0014981 A1* | 1/2005 | Gartside ............. C07C 6/04 585/324 |
| 2006/0293548 A1 | 12/2006 | Spamer et al. |
| 2007/0038010 A1 | 2/2007 | Xie et al. |
| 2007/0225478 A1 | 9/2007 | Querci et al. |
| 2010/0041930 A1 | 2/2010 | Gartside et al. |
| 2010/0234542 A1 | 9/2010 | Blackborow et al. |
| 2011/0021858 A1 | 1/2011 | Ramachandran et al. |
| 2011/0152595 A1 | 6/2011 | Takai et al. |
| 2011/0196185 A1 | 8/2011 | Krawczyk et al. |
| 2012/0108864 A1 | 5/2012 | Gartside et al. |
| 2012/0264990 A1 | 10/2012 | Nicholas et al. |
| 2012/0283090 A1 | 11/2012 | Popp et al. |
| 2012/0289617 A1 | 11/2012 | Wang et al. |
| 2013/0085311 A1 | 4/2013 | Youn et al. |
| 2015/0141721 A1 | 5/2015 | Choi et al. |
| 2017/0001925 A1 | 1/2017 | Abudawoud et al. |
| 2017/0001926 A1 | 1/2017 | Shaikh et al. |
| 2018/0057425 A1 | 3/2018 | Shaikh et al. |

FOREIGN PATENT DOCUMENTS

| | | |
|---|---|---|
| CN | 101531558 B | 4/2013 |
| CN | 102325742 B | 7/2014 |
| CN | 104370676 A | 2/2015 |
| DE | 10013253 A1 | 9/2001 |
| EP | 304515 B1 | 12/1991 |
| WO | 9929805 A1 | 6/1999 |
| WO | 2006089957 A1 | 8/2006 |
| WO | 2009117128 A1 | 9/2009 |
| WO | 2010019595 A2 | 2/2010 |
| WO | 2011136983 A1 | 11/2011 |
| WO | 2015055594 A1 | 4/2015 |
| WO | 2017003812 A1 | 1/2017 |
| WO | 2017003817 A1 | 1/2017 |
| WO | 2017003821 A1 | 1/2017 |

OTHER PUBLICATIONS

Awayssa et al., "Modified HZSM-5 as FCC Additive for Enhancing Light Olefins Yield from Catalytic Cracking of VGO", Applied Catalysis A: General, 2014, 172-183, 477.

Balcar, et al., "Mesoporous molecular sieves as advanced supports for olefin metathesis catalysts", Coordination chemistry Reviews 257, 2013, pp. 3107-3124, Czech Republic.

Barrett et al., "The Determination of Pore Volume and Area Distributions in Porous Substances. I. Computations from Nitrogen Isotherms", J. Am. Chem. Soc., 1951, 373-380, 73(1).

Beck et al., "A New Family of Mesoporous Molecular Sieves Prepared with Liquid Crystal Templates", J. Am. Chem. Soc., 1992, 10834-10843, 114, American Chemical Society.

Bhuiyan et al., "Kinetics Modelling of 2-Butene Metathesis Over Tungsten Oxide Containing Mesoporous Silica Catalyst", The Canadian Journal of Chemical Engineering, 2014, 1271-1282. 92.

Bhuiyan et al., "Metathesis of 2-Butene to Propylene over W-Mesoporous Molecular Sieves: A Comparative Study Between Tungsten Containing MCM-41 and SBA-15", Applied Catalysis A: General, 2013, 224-234, 467, Elsevier B.V.

Bin Hu, et al., "Highly Active Doped Mesoporous KIT-6 Catalysts for Metathesis of 1-Butene and Ethene to Propene: The Influence of Neighboring Environment of W Species", The Journal of Physical Chemistry, ACS Publication, 2013 American Chemical Society, pp. 26385-26395, USA.

Daniell et al., Enhanced Surface Acidity in Mixed Alumina-Silicas: A Low-Temperature FTIR Study:, 2000, 196, 247-260, Elsevier.

Do et al., "Zeolite Nanoclusters Coated onto the Mesopore Walls of SBA-15", J. Am. Chem. Soc., 2004, 14324-14325, 126, American Chemical Society.

International Search Report and Written Opinion dated Nov. 11, 2016 pertaining to International Application No. PCT/US2016/039025.

International Search Report and Written Opinion dated Sep. 14, 2016 pertaining to International Application No. PCT/US2016/039012.

International Search Report and Written Opinion dated Sep. 27, 2016 pertaining to International Application No. PCT/US2016/0038967.

International Search Report and Written Opinion dated Sep. 14, 2016 pertaining to International Application No. PCT/US2016/039013.

Jermy et al., "Utilization of ZSM-5/MCM-41 Composite as FCC Catalyst Additive for Enhancing Propylene Yield from VGO Cracking", J. Porous Mater, 2012, 499-509, 19, Springer.

Kawai et al., "Metaethesis of Halogen-Containing Olefin Over Re2O7/Al2O3 Catalyst Promited with Alkylmetal as a Cocatalyst", Journal of Molecular Catalysis A: Chemical, 1998, 133, 51-59.

Kumar et al., "Performance of Nano Crystalline H-ZSM-5 As Additive in FCC Catalyst: C Review", International Journal of Research in Engineering and Tehnology, May 2014, vol. 3, pp. 481-485.

Lwin et al., "Olefin Metathesis by Supported Metal Oxide Catalysts", ACS Catalysis, 2014, 2505-2520, 4, American Chemical Society.

Office Action pertaining to U.S. Appl. No. 15/190,950 dated Sep. 27, 2017.

Office Action pertaining to U.S. Appl. No. 15/190,964 dated Nov. 2, 2017.

Quignard et al., "Aryloxide Ligands in Metathesis of Olefins and Olefinic Esters: Catalytic Behaviour ofW(OAr)2Cl4 by SnMe4, Sn(n-Bu)4, Pb(n-Bu)4, MgNp2: synthesis of W(OAr)2Cl2(CHCMe3)(OR2) and W(OAr)2Cl(CHCMe3)(CH2CMe3)(OR2)", Journal of Molecular Catalysis, 1986, 36, 13-29.

(56) References Cited

OTHER PUBLICATIONS

Ruihua Gao, et al., "High-activity, single-site mesoporous WO3-MCF materials for the catalytic epoxidation of cycloocta-1, 5-diene with aqueous hydrogen peroxide", Journal of Catalysis, 256, 2008, pp. 259-267, China.

Wang et al., "Synthesis and Structure of Silicalite-1/SBA-15 Composites Prepared by Carbon Templating and Crystallization", Journal of Materials Chemistry, 2007,4265-4273,17, The Royal Society of Chemistry 2007.

Wang et al., "Effect of Support Nature on WO3/SiO2 Structure and Butene-1 Metathesis", Applied Catalysis A: General, 2003, 25-37, 250, Elsevier B.V.

Zhao et al., "Effect of Tungsten Oxide Loading on Metathesis Activity of Ethene and 2-Butene Over WO3/SiO2 catalysts" Transition Met Chem, 2009, 621-27, 34, Springer.

International Preliminary Report on Patentability dated Jan. 1, 2018—PCT/US2016/039012.

International Preliminary Report on Patentability dated Jan. 2, 2018—PCT/US2016/039012.

Non-Final Office Action pertaing to U.S. Appl. No. 15/398,196 dated Jan. 9, 2018.

Puriwat, et al., "Elucidation of the basicity dependence of 1-butene isomerization on MgO/Mg(OH)s catalysts", Catalysis Communications, 2010, pp. 80-85.

"International Search Report and Written opinion dated Mar. 28, 2018, pertaining to International Application No. PCT/US2018/013945, filed Jan. 17, 2018, 9 pages".

U.S. Office Action dated Apr. 20, 2018 pertaining to U.S. Appl. No. 15/859,794, filed Jan. 2, 2018.

International Search Report and Written Opinion dated Apr. 24, 2018 pertaining to International Application No. PCT/US2018/014131, filed Jan. 18, 2018.

Notice of Allowance dated Apr. 24, 2018 pertaining to U.S. Appl. No. 15/190,964, filed Jun. 23, 2016.

Election/Restriction Requirement dated May 21, 2018, pertaining to U.S. Appl. No. 15/866,772, filed Jan. 10, 2018.

Korean Office Action pertaining to Korea Application No. 10-2018-7003238 dated May 14, 2018 (English Translation).

Office Action pertaining to U.S. Appl. No. 15/866,800 dated Jun. 29, 2018.

Office Action pertaining to U.S. Appl. No. 15/190,981 dated Apr. 4, 2017.

Office Action pertaining to U.S. Appl. No. 15/866,772 dated Aug. 28, 2018.

Harmse et al., "On the Product Formation in 1-Butene Methathesis over Supported Tungsten Catalysts", Catal. Lett, vol. 137, pp. 123-131, Apr. 2010.

Shaikh et al., "Self-Methathesis of Butenes to Propylene", Catalysis in Petroleum Refining & Petrochemicals, pp. 1-6, Dec. 7-8, 2015.

Debecker et al., "Preparation of Mo03/sI02-Al203 methathesis catalysts via wet impregnation with different Mo precursors", Journal of Molecular Catalysis A: Chemical, 340, pp. 65-76, 2011.

Wu et al., "Investigation on acidity of zeolites bound with silica and alumina", Studies in Surface Science and Catalysis, 143, pp. 217-225, 2002.

Examination Report pertaining to GCC Application No. 2016/31672 dated Sep. 13, 2018.

* cited by examiner

SYSTEMS AND METHODS FOR PRODUCING PROPYLENE

CROSS REFERENCE TO RELATED APPLICATIONS

This application is a divisional application of U.S. patent application Ser. No. 15/190,964 filed Jun. 23, 2016 which claims priority to U.S. Provisional Application Ser. No. 62/188,052 filed Jul. 2, 2015, and the entire disclosure of each are hereby incorporated by reference herein.

BACKGROUND

Field

The present disclosure generally relates to processes and systems for producing propylene, and more specifically, to processes and systems for producing propylene from process streams comprising butene.

Technical Background

In recent years, there has been a dramatic increase in the demand for propylene to feed the growing markets for polypropylene, propylene oxide, and acrylic acid. Currently, most of the propylene produced worldwide is a byproduct from steam cracking units which primarily produce ethylene, or a by-product from FCC units which primarily produce gasoline. These processes cannot respond adequately to a rapid increase in propylene demand.

Other propylene production processes contribute to the total propylene production. Among these processes are propane dehydrogenation (PDH), metathesis reactions requiring both ethylene and butene, high severity FCC, olefins cracking, and methanol to olefins (MTO). However, propylene demand has increased and propylene supply has not kept pace with this increase in demand.

Regarding the production of propylene by metathesis requiring ethylene and butene, generally, a stoichiometric ratio of about 1 butene to 1 ethylene is desirable for high product yield. However, in some cases, ethylene is not available, or is not available in great enough quantities compared to butene supply. Therefore, such processes requiring butene and ethylene may not be feasible due to lack of ethylene supply available for reaction. Accordingly, an ongoing need exists for a process for efficiently converting butene to propylene, and specifically for efficiently converting butene to propylene without the need for ethylene.

BRIEF SUMMARY

In accordance with one embodiment of the present disclosure, propylene may be produced by a process comprising at least partially metathesizing a first stream comprising butene to form a metathesis-reaction product, at least partially cracking the metathesis-reaction product to produce a cracking-reaction product comprising propylene, and at least partially separating propylene from the cracking-reaction product to form a product stream comprising propylene.

In accordance with another embodiment of the present disclosure, propylene may be produced by a process comprising introducing a first stream comprising butene to a reactor, at least partially metathesizing the first stream with a metathesis catalyst to form a metathesis-reaction product, at least partially cracking the metathesis-reaction product with the cracking catalyst to form a cracking-reaction product, passing the cracking-reaction product out of the reactor in a cracking-reaction product stream, and at least partially separating propylene from the cracking-reaction product stream to form a product stream comprising propylene. The reactor may comprise a metathesis catalyst and a cracking catalyst, the metathesis catalyst positioned generally upstream of the cracking catalyst.

In accordance with yet another embodiment of the present disclosure, propylene may be produced by a process comprising introducing a first stream comprising butene to a first reactor, at least partially metathesizing the first stream in the first reactor to form a metathesis-reaction product, passing the metathesis-reaction product out of the first reactor in a metathesis-reaction product stream and into a second reactor, at least partially cracking the metathesis-reaction product stream in the second reactor to form a cracking-reaction product, passing the cracking-reaction product out of the second reactor in a cracking-reaction product stream, and at least partially separating propylene from the cracking-reaction product stream to form a product stream comprising propylene. The first reactor may comprise a metathesis catalyst and the second reactor may comprise a cracking catalyst. At least a portion of the butene in the cracking-reaction product stream may be recycled by at least partially separating butene the cracking-reaction product stream to form a recycle stream comprising butene, where the first stream is a mixture of the recycle stream and a system inlet stream.

According to embodiments, metathesis catalysts may be utilized which comprises a mesoporous silica catalyst impregnated with metal oxide, where the mesoporous silica catalyst includes a pore size distribution of about 2.5 nm to about 40 nm and a total pore volume of at least about 0.600 $cm^3/g$. In another embodiment, a cracking catalyst may be utilized which comprises a mordenite framework inverted (MFI) structured silica catalyst, where the MFI structured silica catalyst includes total acidity of 0.001 mmol/g to 0.1 mmol/g. In another embodiment, a cracking catalyst may be utilized which comprises an amorphous mesoporous silica foam impregnated with metal oxides, where the metathesis catalyst has a pore size distribution of at least 3 nm to 40 nm and a total pore volume of at least 0.700 $cm^3/g$.

In accordance with yet another embodiment of the present disclosure, systems may be operable to perform the processes for producing propylene described in this disclosure.

Additional features and advantages of the technology disclosed in this disclosure will be set forth in the detailed description which follows, and in part will be readily apparent to those skilled in the art from the description or recognized by practicing the technology as described in this disclosure, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
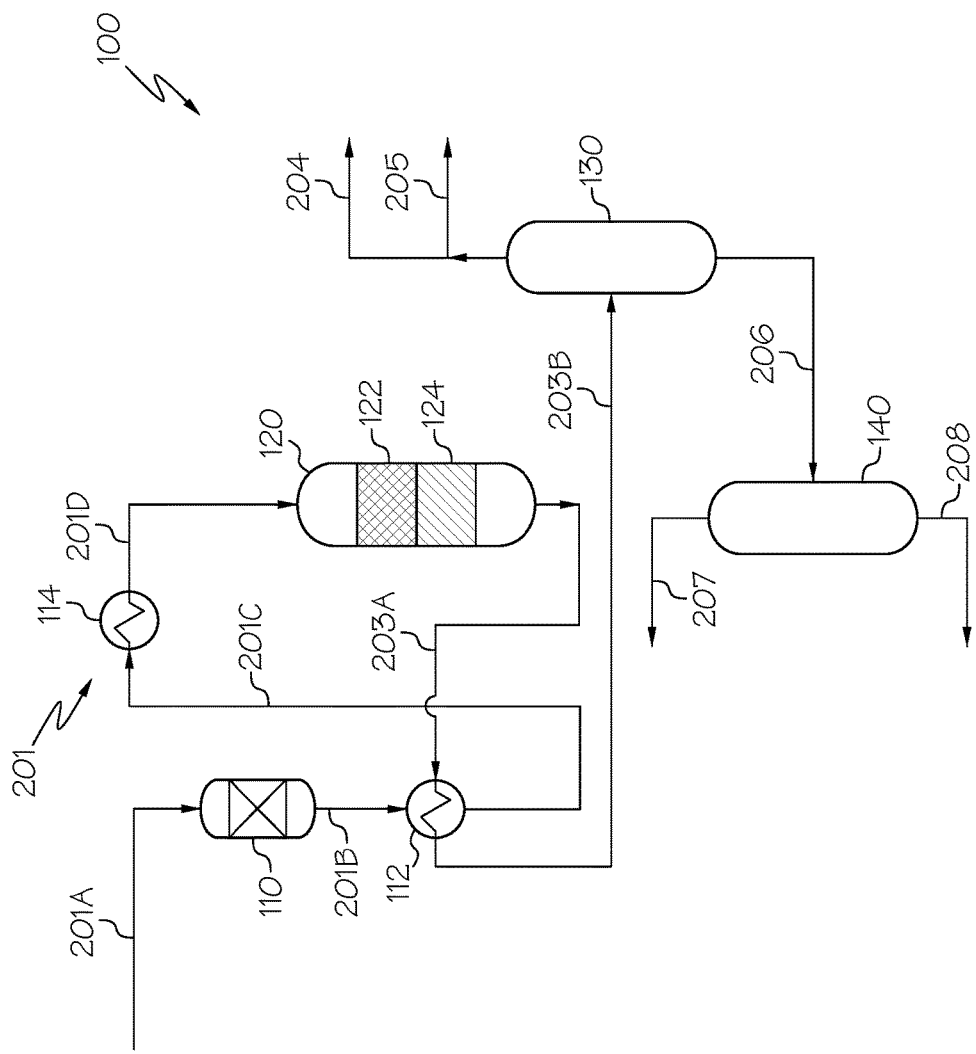
FIG. 1 is a generalized diagram of a butene conversion system comprising a dual catalyst reactor, according to one or more embodiments described in this disclosure.

For the purpose of the simplified schematic illustrations and descriptions of FIGS. 1-4, the numerous valves, temperature sensors, electronic controllers and the like that may be employed and well known to those of ordinary skill in the art of certain refinery operations are not included. Further, accompanying components that are in conventional refinery operations including catalytic conversion processes such as, for example, air supplies, catalyst hoppers, and flue gas handling are not depicted. However, operational components, such as those described in the present disclosure, may be added to the embodiments described in this disclosure.

It should further be noted that arrows in the drawings refer to transfer lines which may serve to transfer steams between two or more system components. Additionally, arrows that connect to system components define inlets or outlets in each given system component. The arrow direction corresponds generally with the major direction of movement of the materials of the stream contained within the physical transfer line signified by the arrow. Furthermore, arrows which do not connect two or more system components signify a product stream which exits the depicted system or a system inlet stream which enters the depicted system. Product streams may be further processed in accompanying chemical processing systems or may be commercialized as end products. System inlet streams may be streams transferred from accompanying chemical processing systems or may be non-processed feedstock streams.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Generally, described in this disclosure are various embodiments of systems and methods for converting butene into propylene. Generally, the conversion systems include system components which are operable to carry out a method where a stream comprising butene undergoes a metathesis reaction and a cracking reaction to form propylene. In some embodiments, the metathesis reaction may be followed by the cracking reaction, where the metathesis and cracking reactions may be carried out in separate reactors arranged in series or may be carried out in a single reactor comprising multiple catalysts positioned in different sections of the reactor. Following the metathesis and cracking reactions, the product stream may be separated into multiple streams, where some streams may optionally be recycled back into the system. Following a downstream separation process, a product stream comprising at least about 80 wt. % propylene may be produced from the reaction products of the cracking reaction. The systems may operate with a single system inlet stream comprising at least about 50 wt. % butenes, such as raffinate streams created from a naphtha cracking process. The systems generally do not require a system inlet comprising ethylene, and the process is fully functional without ethylene supplied to the system.

As used in this disclosure, "transfer lines" may include pipes, conduits, channels, or other suitable physical transfer lines that connect by fluidic communication one or more system components to one or more other system components. As used in this disclosure, a "system component" refers to any apparatus included in the system, such as, but not limited to, separation units, reactors, heat transfer devices such as heaters and heat exchangers, filters, impurities removal devices, combinations of each, and the like. A transfer line may generally carry a process stream between two or more system components. Generally, a transfer line may comprise multiple segments, where a "segment" of a transfer line includes one or more portions of a transfer line, such that a transfer line may comprise multiple transfer line segments. Generally, the chemical composition of a process stream in a particular transfer line is similar or identical throughout the entire length of the transfer line. However, it should be appreciated that the temperature, pressure, or other physical properties of a process stream may change through a transfer line, particularly in different transfer line segments. Also, relatively minor compositional changes in a process stream may take place over the length of a transfer line, such as the removal of an impurity. Also, sometimes the systems described in this disclosure are referred to as "butene conversion systems," which refers to any system which at least partially converts butene into one or more other chemical species. For example, in some embodiments, butene is at least partially converted into propylene. As described in this disclosure, the butene conversion systems are suitable to process streams comprising butene, including streams that are substantially free of other alkenes (for example, ethylene, propene), into a product process stream comprising a significant amount of propylene. As used in this disclosure, a stream or composition does "not substantially comprise" or "is substantially free" of a component when that component is present in an amount of less than 0.1 wt. %.

As used in this disclosure, a "separation unit" refers to any separation device that at least partially separates one or more chemicals that are mixed in a process stream from one another. For example, a separation unit may selectively separate differing chemical species from one another, forming one or more chemical fractions. Examples of separation units include, without limitation, distillation columns, flash drums, knock-out drums, knock-out pots, centrifuges, filtration devices, traps, scrubbers, expansion devices, membranes, solvent extraction devices, and the like. It should be understood that separation processes described in this disclosure may not completely separate all of one chemical consistent from all of another chemical constituent. It should be understood that the separation processes described in this disclosure "at least partially" separate different chemical components from one another, and that even if not explicitly stated, it should be understood that separation may include only partial separation. As used in this disclosure, one or more chemical constituents may be "separated" from a process stream to form a new process stream. Generally, a process stream may enter a separation unit and be divided, or separated, into two or more process streams of desired composition. Further, in some separation processes, a "light fraction" and a "heavy fraction" may exit the separation unit, where, in general, the light fraction stream has a lesser boiling point than the heavy fraction stream.

As used in this disclosure, a "reactor" refers to a vessel in which one or more chemical reactions may occur between one or more reactants optionally in the presence of one or more catalysts. For example, a reactor may include a tank or tubular reactor configured to operate as a batch reactor, a continuous stirred-tank reactor (CSTR), or a plug flow reactor. Example reactors include packed bed reactors such as fixed bed reactors, and fluidized bed reactors. A reactor may comprise one or more catalyst sections, such as catalyst beds, where a "section" is the area of the reactor which houses a particular catalyst or group of multiple catalysts. In another embodiment, separation and reactions may take place in a reactive separation unit.

As used in this disclosure, a "catalyst" refers to any substance which increases the rate of a specific chemical reaction. Catalysts described in this disclosure may be utilized to promote various reactions, such as, but not limited to, metathesis or cracking reactions, or both. As used in this disclosure, a "metathesis catalyst" increases the rate of a metathesis reaction, and a "cracking catalyst" increases the rate of a cracking reaction. As used in this disclosure "metathesis" generally refers to a chemical reaction where fragments of alkenes (olefins) are redistributed by the scission and regeneration of alkene bonds. Also, as used in this disclosure, "cracking" generally refers to a chemical reaction where a molecule having carbon to carbon bonds is broken into more than one molecule by the breaking of one or more of the carbon to carbon bonds. The resulting cracked molecules may have combined the same number of carbon atoms as the original molecule prior to cracking.

Examples of metathesis catalysts and cracking catalysts are disclosed in co-pending Saudi Aramco U.S. Provisional Patent Application No. 62/188,178 entitled "Dual Catalyst System for Propylene Production" and co-pending Saudi Aramco U.S. Provisional Patent Application No. 62/188,129 entitled "Propylene Production Using a Mesoporous Silica Foam Metathesis Catalyst", each of which are incorporated by reference in their entirety in this disclosure. As noted in those disclosures, suitable metathesis catalysts may include mesoporous silica catalysts impregnated with metal oxide. Suitable cracking catalysts may include mordenite framework inverted (MFI) structured silica catalysts. The mesoporous silica catalysts may include a pore size distribution of from about 2.5 nm to about 40 nm and a total pore volume of at least about 0.600 $cm^3/g$ (cubic centimeters per gram). However, it should be understood that the systems described in this disclosure may include any suitable metathesis catalysts and cracking catalysts, such as commercially available catalysts or catalysts which are the subject of future discovery.

The suitable reaction conditions for metathesis and cracking reactions described in this disclosure may vary by the catalyst compositions employed. However, in some embodiments, the metathesis or cracking reactions, or both, may take place at temperatures from about 500° C. (degrees Celsius) to about 600° C. in atmospheric pressure.

As described in this disclosure, "butene" may include at least 1-butene, isobutene, cis-2-butene, trans-2-butene 2-methyl-2-butene, 3-methyl-1-butene, 2-methyl-1-butene, and cyclobutene. Butene is sometimes referred to as butylene, and the terms "butene" and "butylene" may be used interchangeably in this disclosure. As described in this disclosure, "pentene" may include at least 1-pentene, cis-2-pentene, trans-2-pentene, 4-methyl-trans-2-pentene, cyclopentene, and 2-methyl-2-pentene. As described in this disclosure, "hexene" may include at least trans-2-hexene, trans-3-hexene, cis-3-hexene, and cyclohexene. In this disclosure, certain chemicals may be referred to in shorthand notation, where C2 stands for ethane, C3 stands for propane, C4 stands for ethane, C5 stands for pentane, C6 stands for hexane, C3=stands for propylene (or propene), C4=stands for butene (or butylene), C5=stands for pentene, and C6=stands for hexene.

It should be understood that when two or more process stream are "mixed" or "combined" when two or more lines intersect in the schematic flow diagrams of FIGS. 1-4. Mixing or combining may also include mixing by directly introducing both streams into a like reactor, separation device, or other system component.

Embodiments of methods to convert butene to propylene, and systems to carry out such methods, will now be described. In one embodiment, a butene conversion system may comprise a dual catalyst reactor where metathesis and cracking reactions occur in a single reactor, described subsequently with reference to FIG. 1. Generally, according to the embodiment of FIG. 1, a stream comprising butene enters the system and undergoes a metathesis reaction, followed by a cracking reaction, in a single reactor. In one embodiment, the reactor contains a metathesis catalyst section upstream of a cracking catalyst section. The product stream of the cracking reaction comprises propylene and a product stream comprising propylene may be separated from the product stream of the cracking reaction. The embodiment of FIG. 2 is similar to that of FIG. 1, but comprises a recycle stream. Generally, the recycle stream of FIG. 2 may comprise butane and butene and be mixed with the inlet stream comprising butene. The stream entering the reactor of FIG. 2 may thereby generally contain a greater percentage of butane than that of the embodiment of FIG. 1.

Figure 3:
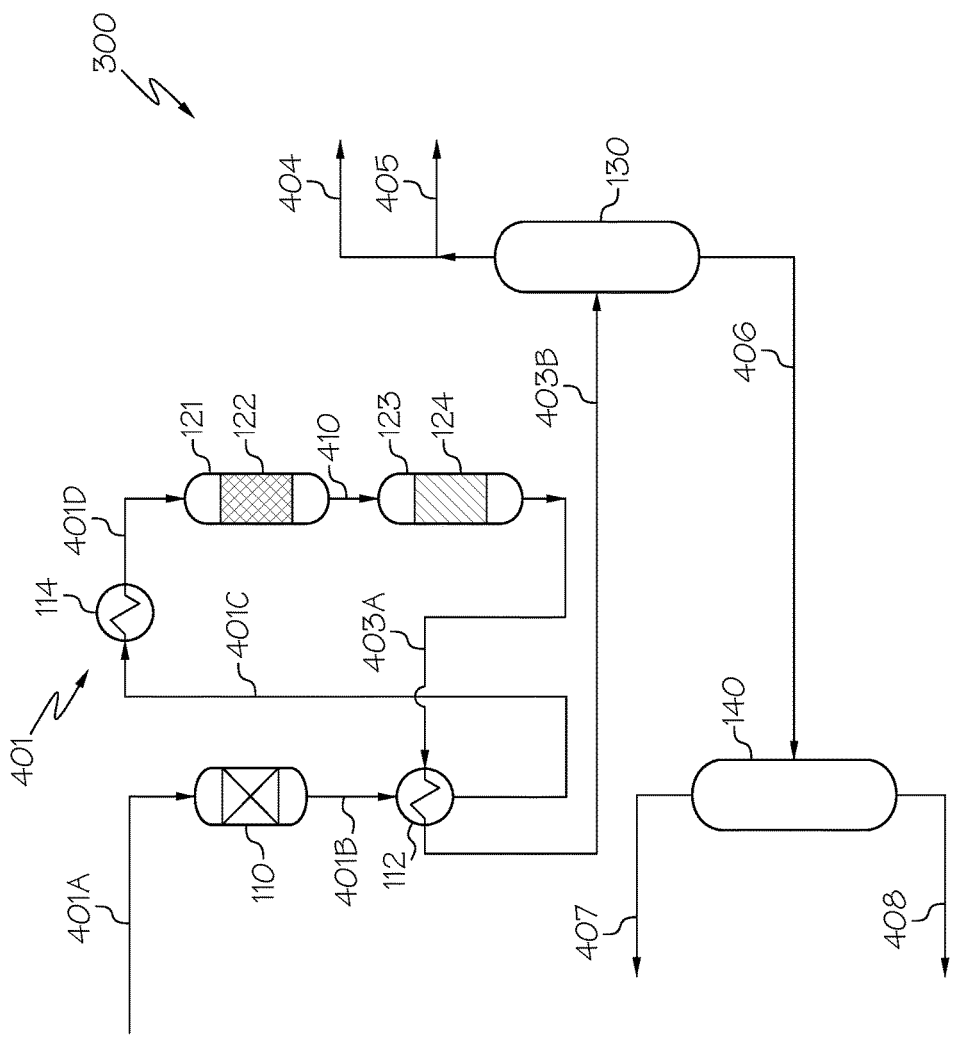
FIG. 3 is a generalized diagram of a butene conversion system comprising reactors in series, according to one or more embodiments described in this disclosure.
Figure 4:
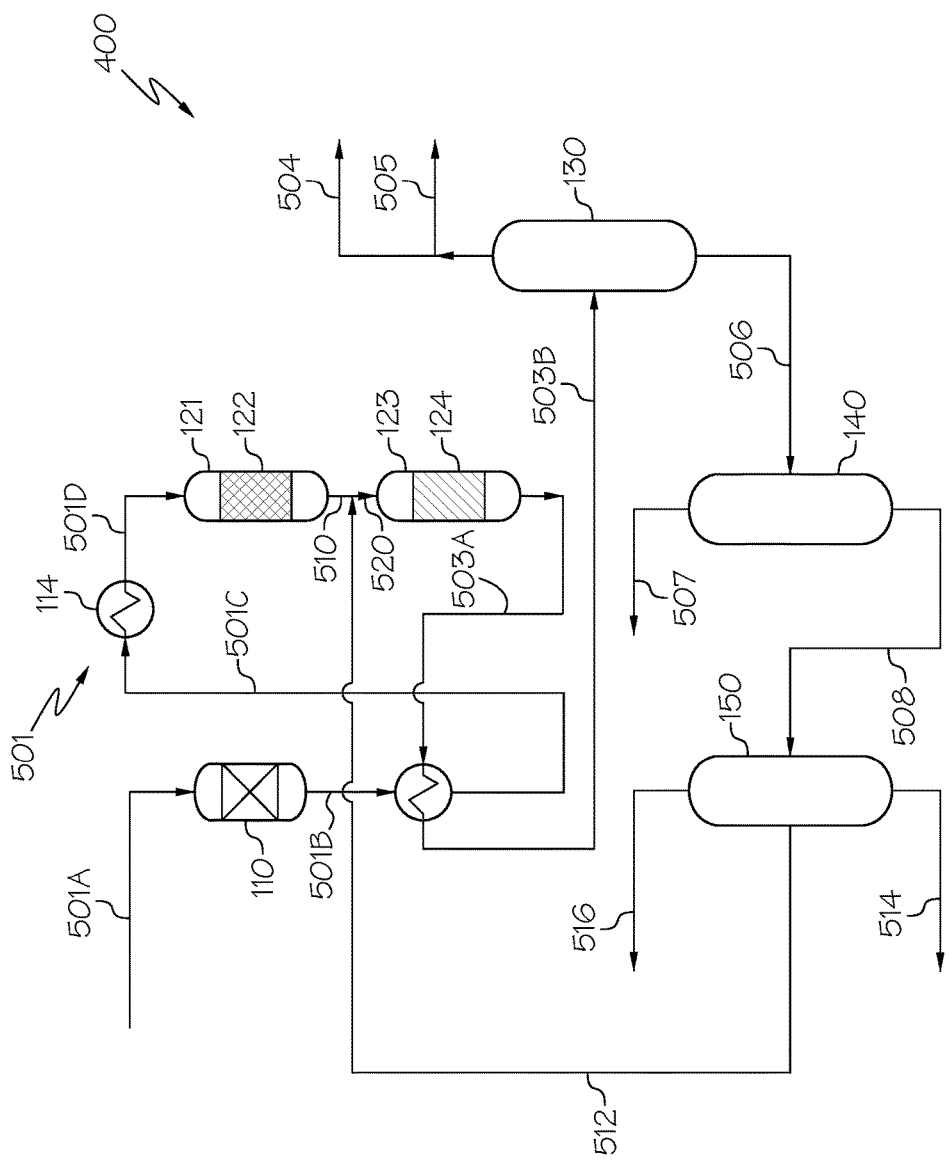
FIG. 4 is a generalized diagram of a butene conversion system comprising reactors in series and a recycle stream, according to one or more embodiments described in this disclosure.
Figure 5:
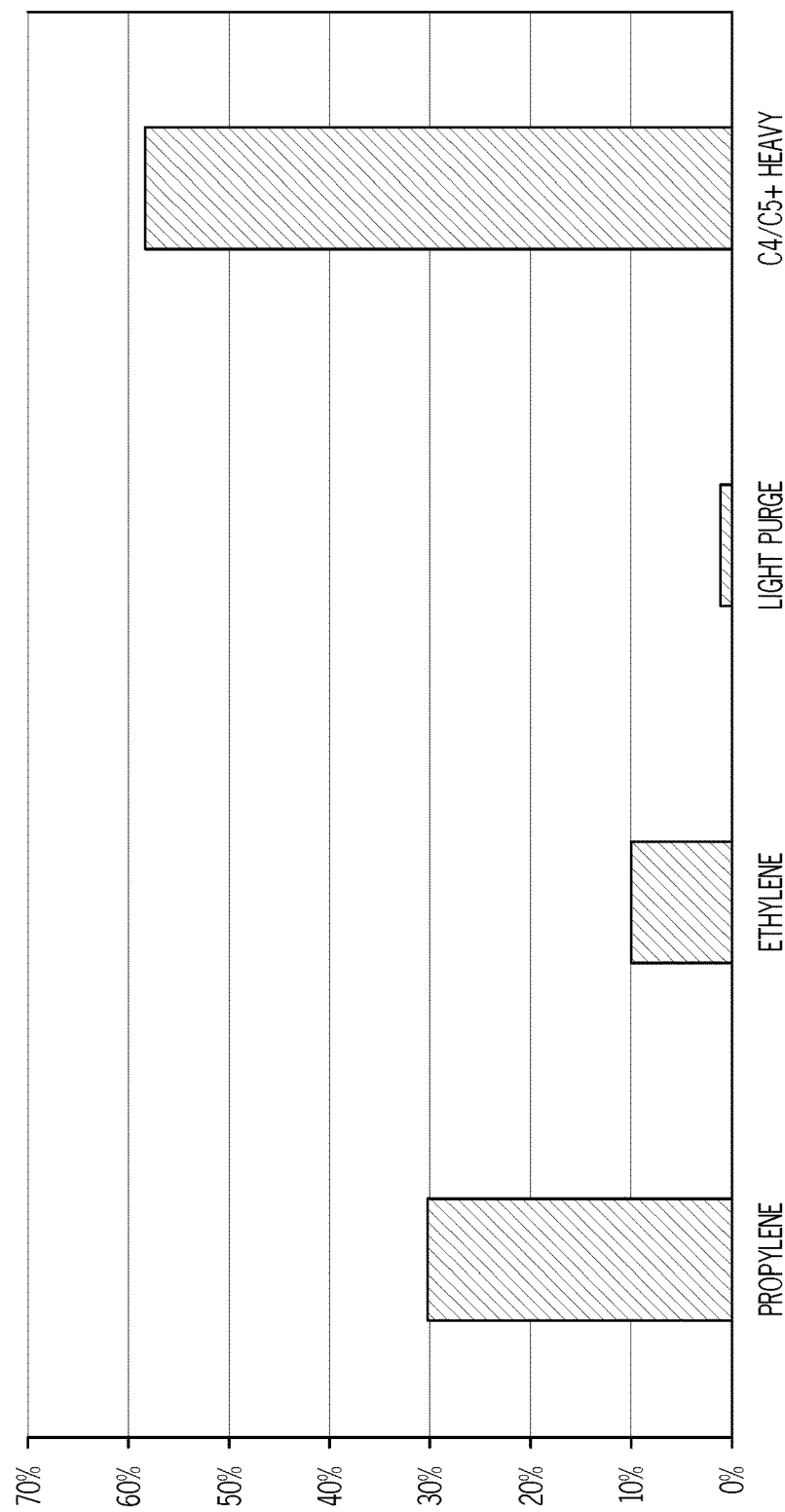
FIG. 5 depicts a bar graph displaying the product distribution in wt. % (weight percent) of the system of FIG. 1, according to one or more embodiments described in this disclosure.

In other embodiments, a butene conversion system may comprise multiple reactors in series where metathesis and cracking reactions occur in separate reactors, as described subsequently with reference to FIGS. 3 and 4. The embodiment of FIG. 3 is similar to that of FIG. 1, but comprises reactors in series in which the metathesis and cracking reactions take place. In general, the stream compositions of FIGS. 1 and 3 may be similar or identical relative to like inlet streams and reaction rates. The embodiment of FIG. 4 is similar to that of FIG. 3, but comprises a recycle stream. Generally, the recycle stream of FIG. 4 may comprise butane and butene and may be mixed with the metathesis-reaction product between the metathesis and cracking reactors.

It should be understood that while the embodiments of FIGS. 1-4 may have varying mechanical apparatus or process stream compositions, or both, these embodiments generally share many of the same system components and transfer lines. As such, processes which occur in like system components in the various embodiments of FIGS. 1-4 may be similar or identical with one another. For example, the system components of FIGS. 1-4 marked with the same reference number may perform similar or identical operations in the various embodiments. Some process streams in the embodiments of FIGS. 1-4 may comprise similar or identical compositions, while others may not. For clarity, the transfer lines of the embodiments of FIGS. 1-4 have each been given different reference numbers so that the composition of their contained stream may be easily identified. However, while some transfer lines may be in like areas and have like functions in the various embodiments of FIGS. 1-4, they may have substantially different compositions (such as in cases where recycle streams are present or where recycle streams reenter at differing system locations). Some process streams contained in like areas of FIGS. 1-4 may be similar or even identical in like processing conditions (for example, like inlet stream composition). For example, the streams of transfer lines/segments such as, but not limited to: 201A, 310, 401A, and 501A may be similar or substantially identical in composition; 204, 304, 404, and 504 may be similar or substantially identical in composition; 205, 305, 405, and 505 may be similar or substantially identical in composition; 207, 307, 407, and 507 may be similar or substantially identical in composition; 203 and 403 may be similar or substantially identical in composition; 206 and 406 may be similar or substantially identical in composition; 208 and 408 may be similar or substantially identical in composition. The Examples, as provided in this disclosure, will help to further clarify the differences in process stream compositions between the various embodiments.

Figure 2:
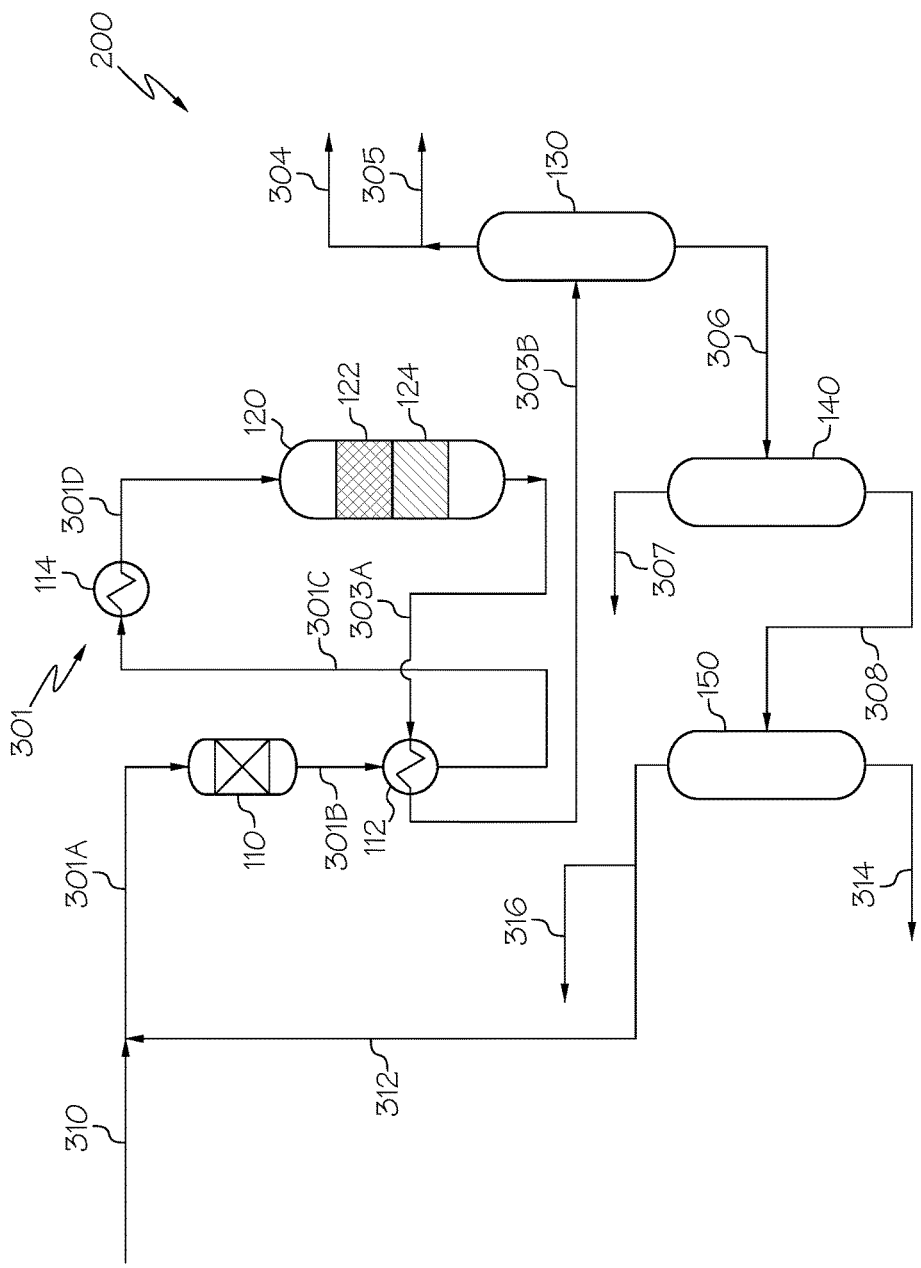
FIG. 2 is a generalized diagram of a butene conversion system comprising a dual catalyst reactor and a recycle stream, according to one or more embodiments described in this disclosure.

Referring now to the process-flow diagram of FIG. 1, in one embodiment, a butene conversion system 100 may include a metathesis/cracking reactor 120 which comprises a metathesis catalyst section 122 and a cracking catalyst section 124. Generally, a system inlet stream comprising butene enters the butene conversion system 100 through a transfer line 201 (including segments 201A, 201B, 201C, and 201D) and is injected into the metathesis/cracking reactor 120. The system inlet stream of segment 201A generally comprises at least butene, and may optionally comprise other chemical species such as butane. For example, the system inlet stream may comprise at least about 20 wt. %, 30 wt. %, 40 wt. %, 50 wt. %, 55 wt. %, 60 wt. %, 65 wt. %, or even at least about 70 wt. % butene. The system inlet stream may comprise at least about 15 wt. %, 20 wt. %, 25 wt. %, 30 wt. %, or even at least about 35 wt. % butane. The system inlet stream may comprise from 0 wt. % to about 10 wt. %, 8 wt. %, 4 wt. %, 2 wt. %, or 1 wt. % ethylene, or may not substantially comprise ethylene.

The system inlet stream may be processed by one or more system components prior to entering the metathesis/cracking reactor 120. In such embodiments, the transfer line 201 may comprise several segments (depicted as 201A, 201B, 201C, and 201D) which may be separated by system components such as an impurities removal device 110, heat transfer device 112, and heat transfer device 114. The impurities removal device 110 may remove oxygenates present in the system inlet stream. In one embodiment, the impurities removal device 110 comprises a catalytic bed. Heat transfer device 112 may be a heat exchanger that serves to elevate the temperature of the system inlet stream by exchanging energy with the stream present in transfer line 203A. Heat transfer device 114 may be a heater that serves to further heat the system inlet stream. It should be understood that the impurities removal device 110, heat transfer device 112, and heat transfer device 114 are optional components in the butene conversion system 100. It should be understood that all streams located in the various segments of transfer line 201 (that is, 201A, 201B, 201C, and 201D) are considered portions of the system inlet stream, even though the chemical composition, temperature, or other properties of the system inlet stream may be different in the various segments 201A, 201B, 201C, 201D.

Still referring to FIG. 1, the metathesis/cracking reactor 120 comprises a metathesis catalyst section 122 and a cracking catalyst section 124. The metathesis catalyst section 122 is positioned generally upstream of the cracking catalyst section 124, that is, the cracking catalyst section 124 is positioned generally downstream of the metathesis catalyst section 122. The system inlet stream from segment 201D enters the metathesis/cracking reactor 120 and contacts the metathesis catalyst to undergo a metathesis reaction in the metathesis catalyst section 122 to form a metathesis-reaction product. Following the metathesis reaction, the metathesis-reaction product is contacted with the cracking catalyst to undergo cracking a cracking reaction in the cracking catalyst section 124. The cracking reaction forms a cracking-reaction product. Generally, the reactants that undergo cracking or metathesis, or both, intimately intermingle with the respective catalysts during reaction.

As used in this disclosure, a "metathesis-reaction product" refers to the entire product mixture resulting from the metathesis reaction, including any portion of the product mixture which does not undergo metathesis. Additionally, as used in this disclosure "cracking-reaction product" refers to the entire product mixture resulting from the cracking reaction, including any portion of the product mixture which does not undergo cracking. For example, the cracking-reaction product include all components of the process stream leaving the reactor where cracking took place.

The cracking-reaction product is passed out of the metathesis/cracking reactor 120 in a cracking-reaction product stream via transfer line 203. The cracking-reaction product may comprise, consist, or consist essentially of a mixture of alkanes and alkenes, including, but not limited to, ethylene, propylene, butene, pentene, hexene, heptene, ethane, propane, butane, pentane, hexane, and heptane. The cracking-reaction product may comprise at least about 2 wt. %, 4 wt. %, 6 wt. %, 8 wt. %, 10 wt. %, 12 wt. %, 14 wt. %, 16 wt. %, 18 wt. %, 20 wt. %, 22 wt. %, 24 wt. %, 26 wt. %, 28 wt. %, or even at least about 30 wt. % propylene.

The cracking-reaction product stream of transfer line 203A formed in the metathesis/cracking reactor 120 may be separated into one or more streams having desired compositions. Generally, a product stream comprising propylene, such as shown in transfer line 207 in FIG. 1, may be formed by separating the cracking-reaction product stream. The product stream may comprise at least about 50 wt. %, 60 wt. %, 70 wt. %, 80 wt. %, 90 wt. %, 95 wt. %, 96 wt. %, 97 wt. %, 98 wt. %, or even at least about 99 wt. % propylene. It should be understood that a wide variety of separation processes may be utilized to produce the product stream comprising propylene.

In one embodiment, as shown in FIG. 1 the cracking-reaction product may be passed to one or more separation units via transfer line 203 which may be comprised of segment 203A and segment 203B, where the segments are divided by heat transfer device 112. The cracking-reaction product may enter separation unit 130 where light constituents, such as ethylene and ethane may be removed. Light constituents such as ethylene may be purged from the butene conversion system 100 via transfer line 204 or may be utilized in other chemical systems via transfer line 205. The streams contained in transfer line 204 and transfer line 205 may comprise, consists, or consist essentially of ethylene. For example, the stream of transfer line 204 or transfer line 205, or both, may comprise at least about 50 wt. %, 60 wt. %, 70 wt. %, 80 wt. %, 90 wt. %, 95 wt. %, 96 wt. %, 97 wt. %, 98 wt. %, or even at least about 99 wt. % ethylene. The heavy fraction from separation unit 130 may be passed out of separation unit 130 via transfer line 206. The process stream of transfer line 206 may comprise a mixture of alkanes and alkenes, including, but not limited to, one or more of propylene, butene, pentene, hexene, heptene, ethane, propane, butane, pentane, hexane, and heptane. The process stream of transfer line 206 may enter separation unit 140 where propylene is separated from other constituents. The light fraction (that is, propylene) may exit the separation unit 140 via transfer line 207 as a propylene product stream. The propylene product stream contained in transfer line 207 may comprise, consists, or consist essentially of propylene. For example, the stream of transfer line 204 or transfer line 205, or both, may comprise at least about 50 wt. %, 60 wt. %, 70 wt. %, 80 wt. %, 90 wt. %, 95 wt. %, 96 wt. %, 97 wt. %, 98 wt. %, or even at least about 99 wt. % propylene. The heavy fraction from separation unit 140 may be passed out of separation unit 140 via transfer line 208. The process stream of line 208 may comprise a mixture of alkanes and alkenes, including, but not limited to, one or more of butene, pentene, hexene, heptene, propane, butane, pentane, hexane, and heptane. The stream of transfer line 208 may be purged from the butene conversion system 100 as an end product or may be further separated in downstream processing.

As referred to previously, the embodiment of FIG. 2 is similar to that of FIG. 1, but comprises a recycle stream majorly comprising butane and butene. Generally, in the embodiment of FIG. 2, the recycle stream of transfer line 312 may comprise butane and butene and be mixed with the inlet stream of transfer line 310 which comprises butene. The stream of transfer line segment 301D enters the reactor and may thereby generally contain a greater percentage of butane than the stream of transfer line segment 201D of FIG. 1. Generally, the addition of the recycle stream as described with reference to FIG. 2 may increase propylene selectivity and propylene yield.

Referring now to the process-flow diagram of FIG. 2, in one embodiment, a butene conversion system 200 may include a metathesis/cracking reactor 120 which comprises a metathesis catalyst section 122 and a cracking catalyst section 124. Generally, a system inlet stream comprising butene enters the butene conversion system 200 through transfer line 310. The system inlet stream of transfer line 310 may generally comprises at least butene, and may optionally comprise other chemical species such as butane. For example, the system inlet stream of transfer line 310 may comprise at least about 20 wt. %, 30 wt. %, 40 wt. %, 50 wt. %, 55 wt. %, 60 wt. %, 65 wt. %, or even at least about 70 wt. % butene, and may comprise at least about 15 wt. %, 20 wt. %, 25 wt. %, 30 wt. %, or at least about 35 wt. % butane. The system inlet stream of transfer line 310 may comprise from 0 wt. % to about 10 wt. %, 8 wt. %, 4 wt. %, or 2 wt. % ethylene, or may not substantially comprise ethylene.

The system inlet stream in transfer line 310 is combined with a recycle stream in transfer line 312 to form a mixed stream present in transfer line 301. The mixed stream is passed through transfer line 301 and is introduced into the metathesis/cracking reactor 120. In embodiments, the recycle stream of transfer line 312 may comprise butene and butane. For example, the recycle stream of transfer line 312 may comprise at least about 5 wt. %, 10 wt. %, 15 wt. %, or even at least about 20 wt. % butene, and may comprise at least about 50 wt. %, 60 wt. %, 70 wt. %, or even greater than about 80 wt. % butane. The recycle stream of transfer line 312 may comprise at least about 80 wt. %, 90 wt. % or even at least about 95 wt. % of the combination of butane and butene.

The mixed stream of transfer line 301 may comprise butane and butene. For example, the mixed stream of transfer line 301 may comprise at least about 5 wt. %, 10 wt. %, 15 wt. %, 20 wt %, 25 wt. %, 30 wt. %, or even at least about 35 wt. % butene, and may comprise at least about 40 wt. %, 50 wt. %, 60 wt. %, 70 wt. %, or even at least about 80 wt. % butane. The mixed stream of transfer line 301 may comprise at least about 80 wt. %, 90 wt. % or even at least about 95 wt. % of the combination of butane and butene.

The mixed stream may be processed by one or more system components prior to entering the metathesis/cracking reactor 120. In such embodiments, the transfer line 301 may comprise several segments (depicted as 301A, 301B, 301C, and 301D) which may be separated by system components such as an impurities removal device 110, heat transfer device 112, and heat transfer device 114.

Following the metathesis and cracking reactions in reactor 120, the cracking-reaction product of transfer line segment 303A may comprise, consist, or consist essentially of a mixture of alkanes and alkenes, including, but not limited to, one or more of ethylene, propylene, butene, pentene, hexene, heptene, ethane, propane, butane, pentane, hexane, and heptane. For example, the cracking-reaction product of the embodiment of FIG. 2 may comprise at least about 2 wt. %, 4 wt. %, 6 wt. %, 8 wt. %, 10 wt. %, 12 wt. %, 14 wt. %, 16 wt. %, 18 wt. %, or even at least about 20 wt. % propylene.

As is described with reference to the embodiment of FIG. 1, the cracking-reaction product of the embodiment of FIG. 2, formed in the metathesis/cracking reactor 120, may be separated into one or more streams having desired compositions. Generally, a product stream comprising propylene (of transfer line 307) may be formed by separating propylene from the cracking-reaction product stream of transfer line 303A. The product stream of transfer line 307 may comprise at least about 50 wt. %, 60 wt. %, 70 wt. %, 80 wt. %, 90 wt. %, 95 wt. %, 96 wt. %, 97 wt. %, 98 wt. %, or even at least about 99 wt. % propylene. It should be understood that a wide variety of separation processes may be utilized to produce the product stream comprising propylene.

In one embodiment, as shown in FIG. 2, the cracking-reaction product may be introduced into one or more separation units via transfer line 303 which may be comprised of segment 303A and segment 303B, where the segments are divided by heat transfer device 112. Similar to the embodiment of FIG. 1 described previously, the cracking-reaction product may enter separation unit 130 where ethylene and other light constituents may be at least partially removed. Following the ethylene separation by separation device 130, propylene may be separated from the heavy fraction of separation unit 130 in separation unit 140. The heavy fraction from separation unit 140 may be passed out of separation unit 140 via transfer line 308. The stream of line 308 may comprise a mixture of alkanes and alkenes, including, but not limited to, one or more of butene, pentene, hexene, heptene, propane, butane, pentane, hexane, and heptane.

The process stream of transfer line 308 may be injected into separation unit 150 where one or more fractions may be separated from one another. In one embodiment, a heavy fraction may exit separation unit 150 in a stream contained in transfer line 314. The stream of transfer line 314 may comprise one or more of pentene, pentane, hexene, heptene, pentane, hexane, and heptane. The light fraction of separation unit 150, which comprises primarily butene and butane, may exit separation unit 150 in the recycle stream contained in transfer line 312. A portion of the recycle stream contained in transfer line 312 may be purged from the system 200 via transfer line 316. The remaining portion may be recycled into the system 200 by combining the stream of transfer line 312 with the system inlet stream of transfer line 310.

In another embodiment, as described with reference to FIG. 3, a butene conversion system 300 may comprise multiple reactors in series where metathesis and cracking reactions occur in separate reactors. The embodiment of FIG. 3 is similar to that of FIG. 1, but comprises separate metathesis and catalyst reactors in series. In some embodiments, it may be advantageous to utilize reactors in series, such as when the metathesis reaction and cracking reaction are performed at different reaction conditions (such as different temperature or/and pressure). The other system components (non-reactor) of FIG. 3 may generally be similar or identical to those described with reference to FIG. 1. The embodiment of FIG. 3 may result in similar or identical butene conversion, propylene selectivity, and propylene yield as compare with the embodiment of FIG. 1. Additionally, the compositions of the process streams of the embodiment of FIG. 3 may be similar or identical to those of FIG. 1.

Referring now to the process-flow diagram of FIG. 3, in one embodiment, a butene conversion system 300 may include a metathesis reactor 121, which comprises a metathesis catalyst section 122, and a cracking reactor 123, which comprises a cracking catalyst section 124. Generally, a system inlet stream comprising butene enters the butene conversion system 300 through a transfer line 401 and is injected into the metathesis reactor 121. The system inlet stream generally comprises at least butene, and may optionally comprise other chemical species such as butane. For example, the system inlet stream of transfer line 401 may comprise at least about 20 wt. %, 30 wt. %, 40 wt. %, 50 wt. %, 55 wt. %, 60 wt. %, 65 wt. %, or even at least about 70 wt. % butene. The system inlet stream may comprise at least about 15 wt. %, 20 wt. %, 25 wt. %, 30 wt. %, or even at least about 35 wt. % butane.

Still referring to FIG. 3, the metathesis reactor 121 comprises a metathesis catalyst section 122, such as a metathesis catalyst bed, and the cracking reactor 123 comprises a cracking catalyst section 124, such as a cracking catalyst bed. The metathesis reactor 121 and the cracking reactor 123 are arranged in series where the metathesis reactor 121 is positioned generally upstream of the cracking reactor 123, that is, the cracking reactor 123 is positioned generally downstream of the metathesis reactor 121. The system inlet stream from segment 401D enters the metathesis reactor 121 and undergoes a metathesis reaction in the metathesis catalyst section 122 to form a metathesis-reaction product. The metathesis-reaction product may be passed out of the metathesis reactor in a metathesis-reaction product stream via transfer line 410. The metathesis-reaction product stream enters the cracking reactor 123 and is cracked in a cracking reaction in the cracking catalyst section 124. The cracking reaction forms a cracking-reaction product. The cracking-reaction product is passed out of the cracking reactor 123 in a cracking-reaction product stream via transfer line 403. The cracking-reaction product may comprise, consist, or consist essentially of a mixture of alkanes and alkenes, including, but not limited to, one or more of ethylene, propylene, butene, pentene, hexene, heptene, ethane, propane, butane, pentane, hexane, and heptane. The cracking-reaction product may comprise at least about 2 wt. %, 4 wt. %, 6 wt. %, 8 wt. %, 10 wt. %, 12 wt. %, 14 wt. %, 16 wt. %, 18 wt. %, 20 wt. %, 22 wt. %, 24 wt. %, 26 wt. %, 28 wt. %, or even at least about 30 wt. % propylene.

Similar to the embodiment of FIG. 1, in the embodiment of FIG. 3 the cracking-reaction product may be separated into one or more streams having desired compositions. Generally, a product stream comprising propylene (in transfer line 407) may be formed by separating propylene from the other components of the cracking-reaction product stream. The product stream of transfer line 407 may comprise at least about 50 wt. %, 60 wt. %, 70 wt. %, 80 wt. %, 90 wt. %, 95 wt. %, 96 wt. %, 97 wt. %, 98 wt. %, or even at least about 99 wt. % propylene. It should be understood that a wide variety of separation processes may be utilized to produce the product stream comprising propylene. As shown in FIG. 3, multiple separation units may be utilized.

Now with reference to FIG. 4, the embodiment of FIG. 4 is similar to that of FIG. 3, but comprises a recycle stream in transfer line 512. Generally, the recycle stream of FIG. 3 (in transfer line 512) may comprise butane and butene and may be mixed with the metathesis-reaction product stream in transfer line 510, located between the metathesis reactor 121 and cracking reactor 123.

Still referring to the process-flow diagram of FIG. 4, in one embodiment, a butene conversion system 400 may include a metathesis reactor 121 which comprises a metathesis catalyst section 122 and a cracking reactor 123 which comprises a cracking catalyst section 124. Generally, a system inlet stream comprising butene enters the butene conversion system 400 through a transfer line 501 and is injected into the metathesis reactor 121. The system inlet stream generally comprises at least butene, and may optionally comprise other chemical species such as butane. For example, the system inlet stream may comprise at least about 20 wt. %, 30 wt. %, 40 wt. %, 50 wt. %, 55 wt. %, 60 wt. %, 65 wt. %, or even 70 wt. % butene. The system inlet stream may comprise at least about 15 wt. %, 20 wt. %, 25 wt. %, 30 wt. %, or even 35 wt. % butane.

The system inlet stream from segment 501D may enter the metathesis reactor 121 and undergoes a metathesis reaction in the metathesis catalyst section 122 to form a metathesis-reaction product. The metathesis-reaction product may be passed out of the metathesis reactor 121 in a metathesis-reaction product stream via transfer line 510. The metathesis-reaction product stream contained in transfer line 510 is combined with the recycle stream of transfer line 512 to form a mixed stream in transfer line 520. In embodiments, the recycle stream of transfer line 512 may comprise butene and butane. For example, the recycle stream of transfer line 512 may comprise at least about 5 wt. %, 10 wt. %, 15 wt. %, 20 wt. %, 25 wt. %, 30 wt. %, or even at least about 35 wt. % butene, and may comprise at least about 40 wt. %, 50 wt. %, 60 wt. %, 70 wt. %, or even at least about 80 wt. % butane. The recycle stream of transfer line 512 may comprise at least about 80 wt. %, 90 wt. %, or even at least about 95 wt. % of the combination of butane and butene.

The mixed stream of transfer line 520 enters the cracking reactor 123 and is cracked in a cracking reaction in the cracking catalyst section 124. The cracking reaction forms a cracking-reaction product. The cracking-reaction product is passed out of the cracking reactor 123 in a cracking-reaction product stream via transfer line 503. The cracking-reaction product may comprise, consist, or consist essentially of a mixture of alkanes and alkenes, including, but not limited to, one or more of ethylene, propylene, butene, pentene, hexene, heptene, ethane, propane, butane, pentane, hexane, and heptane. The cracking-reaction product may comprise at least about 1 wt. %, 2 wt. %, 3 wt. %, 4 wt. %, 5 wt. %, 6 wt. %, 7 wt. %, 8 wt. %, 10 wt. %, 15 wt. %, or even at least about 20 wt. % propylene.

As described with reference to the embodiments of FIG. 3, the cracking-reaction product (in transfer line 503A) formed in the cracking reactor 123 may be separated into one or more streams having desired compositions. Generally, a product stream comprising propylene (in transfer line 507) may be formed by separating propylene from the other components of the cracking-reaction product stream. The product stream of transfer line 507 may comprise at least about 50 wt. %, 60 wt. %, 70 wt. %, 80 wt. %, 90 wt. %, 95 wt. %, 96 wt. %, 97 wt. %, 98 wt. %, or even at least about 99 wt. % propylene. It should be understood that a wide variety of separation processes may be utilized to produce the product stream comprising propylene.

In one embodiment, as shown in FIG. 4 the cracking-reaction product may be introduced to one or more separation units via transfer line 503 which may be comprised of segment 503A and segment 503B, where the segments are divided by heat transfer device 112. Similar to the embodiment of FIGS. 1 and 3, the cracking-reaction product may enter separation unit 130 where ethylene and other light constituents may be removed. Following the ethylene separation by separation unit 130, propylene may be separated from the heavy fraction of separation unit 130 in separation unit 140. The heavy fraction from separation unit 140 may be passed out of separation unit 140 via transfer line 508. The stream of line 508 may comprise a mixture of alkanes and alkenes, including, but not limited to, one or more of butene, pentene, hexene, heptene, propane, butane, pentane, hexane, and heptane.

The process stream of transfer line 508 may be injected into separation unit 150 where one or more fractions may be separated from one another. In one embodiment, a bottoms fraction may exit separation unit 150 in a stream contained in transfer line 514. The process stream of transfer line 514 may comprise one or more of pentene, pentane, hexene, hexane heptene, and heptane. The light fraction may exit separation unit 150 in a stream contained in transfer line 516 and be purged from the system 400. The stream of transfer line 516 may comprise one or more of butene and butane, for example, at least about 20 wt. %, 30 wt. %, 40 wt. %, or even at least about 50 wt. % butane. A recycle stream contained in transfer line 512 may be recycled into the system 400 by combining the stream of transfer line 512 with the metathesis product stream of transfer line 510. In one embodiment, the recycle stream of 512 may be a portion of the top fraction stream of transfer line 516.

Generally, a stream containing butane and butene, suitable as the inlet stream in the embodiments described in this disclosure, may be produced from refining operations. This stream containing butane and butene may be separated into fractions to form a first raffinate, second raffinate, and third raffinate. In one embodiment, the system inlet stream may be a raffinate stream from an olefin refining system, such as a conventional refinery. The stream produced from the refining operation may generally comprise a C4 alkanes and alkenes, including butanes, butenes, and butadienes. A "first raffinate" may be produced by separating 1,3-butadiene from the other C4 constituents in the stream. The first raffinate may comprise isobutylene, cis-2-butene, and trans-2-butene. For example, the first raffinate may comprise, or consist essentially of, from about 40 wt. % to about 50 wt. %, from about 35 wt. % to about 55 wt. %, or from about 30 wt. % to about 60 wt. % of isobutene and from about 30 wt. % to about 35 wt. %, from about 25 wt. % to about 40 wt. %, or from about 20 wt. % to about 45 wt. % of the sum of cis-2-butene and trans-2-butene. A "second raffinate" may be produced by separating isobutylene from the other C4 constituents of the first raffinate. For example, the second raffinate may comprise, or consist essentially of, from about 50 wt. % to about 60 wt. %, from about 45 wt. % to about 65 wt. %, or from about 40 wt. % to about 70 wt. % of the sum of cis-2-butene and trans-2-butene, from about 10 wt. % to about 15 wt. %, from about 5 wt. % to about 20 wt. %, or from about 0 wt. % to about 25 wt. % of 1-butene, and from about 15 wt. % to about 25 wt. %, from about 10 wt. % to about 30 wt. %, or from about 5 wt. % to about 35 wt. % of butane. The inlet stream of the systems described herein may be substantially free of isobutene, and may consist essentially of 2-butenes and n-butanes.

Referring to embodiments of the catalyzed reactions described herein, as shown in the following Formulas 1 and 2, "metathesis" or "self-metathesis" may generally be a two-step process: 2-butene isomerization and then cross-metathesis using the metathesis catalyst system. As shown in the following Formula 3, in embodiments "catalyzed cracking" may refer to the conversion of $C_4$-$C_6$ alkenes to propylene and other alkanes and/or alkenes, for example, $C_1$-$C_2$ alkenes.

Formula 1: 2-Butene Isomerization

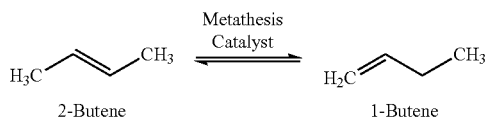

Formula 2: Cross-Metathesis

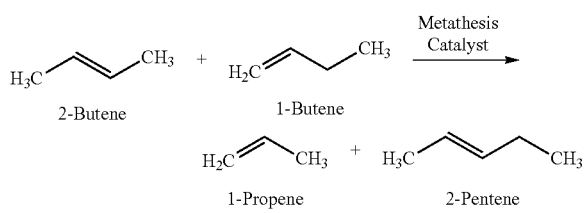

Formula 3: Catalytic Cracking

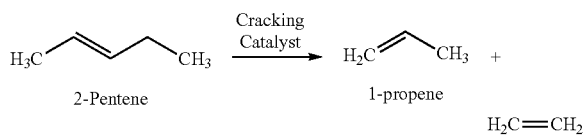

Referring to Formulas 1-3, the "metathesis" and "catalytic cracking" reactions are not limited to these reactants and products; however, Formulas 1-3 provide a basic illustration of the reaction methodology according to some embodiments. As shown in Formulas 1 and 2, metathesis reactions take place between two alkenes. The groups bonded to the carbon atoms of the double bond are exchanged between the molecules to produce two new alkenes with the swapped groups. The specific catalyst that is selected for the olefin metathesis reaction may generally determine whether a cis-isomer or trans-isomer is formed, as the coordination of the olefin molecules with the catalyst play an important role, as do the steric influences of the substituents on the double bond of the newly formed molecule.

In one embodiment, the present dual catalyst system comprises: a mesoporous silica catalyst, which is a mesoporous silica catalyst support impregnated with metal oxide; and a mordenite framework inverted (MFI) structured silica catalyst downstream of the mesoporous silica catalyst. Various structures are contemplated for the mesoporous silica catalyst support, for example, a molecular sieve. As used in the application, "mesoporous" means that the silica support has a narrow pore size distribution. Specifically, the mesoporous silica catalyst includes a narrow pore size distribution of from about 2.5 nm (nanometers) to about 40 nm and a total pore volume of at least about 0.600 $cm^3/g$. Without being bound by theory, the present pore size distribution and pore volume are sized to achieve better catalytic activity and reduced blocking of pores by metal oxides, whereas smaller pore volume and pore size catalyst systems are susceptible to pore blocking and thereby reduced catalytic activity.

Moreover, utilizing an MFI structured silica catalyst downstream of the mesoporous silica catalyst surprisingly provides the best yield of propylene from a butene stream. The person of ordinary skill in the art would have expected the best yield by first cracking butene to propylene and then cracking any remaining butene via metathesis. However, it was surprisingly found that propylene yield is increased, and additionally the combined yield of propylene and ethylene is increased by placing the MFI structured silica catalyst downstream of the mesoporous silica catalyst.

In one or more embodiments, the pore size distribution of the mesoporous silica catalyst may range from about 2.5 nm to about 40 nm, or about 2.5 nm to about 20 nm, or about 2.5 nm to about 4.5 nm, or about 2.5 nm to about 3.5 nm, or about 8 nm to about 18 nm, or about 12 nm to about 18 nm. In further embodiments, the total pore volume may be from about 0.600 $cm^3/g$ to about 2.5 $cm^3/g$, or about 0.600 $cm^3/g$ to about 1.5 $cm^3/g$, or about 0.600 $cm^3/g$ to about 1.3 $cm^3/g$, or about 0.600 $cm^3/g$ to about 0.800 $cm^3/g$, or about 0.600 $cm^3/g$ to about 0.700 $cm^3/g$, or about 0.900 $cm^3/g$ to about 1.3 $cm^3/g$.

Moreover, while broader ranges are contemplated, the mesoporous silica catalyst may, in one or more embodiments, include a surface area of about 250 square meters/gram ($m^2/g$) to about 600 $m^2/g$. In further embodiments, the mesoporous silica catalyst may have a surface area of from about 450 $m^2/g$ to about 600 $m^2/g$, or about 250 $m^2/g$ to about 350 $m^2/g$, or about 275 $m^2/g$ to about 325 $m^2/g$, or about 275 $m^2/g$ to about 300 $m^2/g$. Further, the mesoporous silica catalyst may have a total acidity of up to about 0.5 millimole/gram (mmol/g), or about 0.01 mmol/g to about 0.5 mmol/g, or about 0.1 mmol/g to about 0.5 mmol/g, or about 0.3 mmol/g to about 0.5 mmol/g, or about 0.4 mmol/g to about 0.5 mmol/g. Acidity is generally maintained at or less than about 0.5 mmol/g to yield the desired selectivity of propylene and reduced production of undesirable byproducts such as aromatics. Increasing acidity may increase the overall butene conversion; however, this increased conversion may lead to less selectivity and increased production of aromatic byproducts, which can lead to catalyst coking and deactivation.

Furthermore, the mesoporous silica catalyst may have a particle size of from about 20 nm to about 200 nm, or about 50 nm to about 150 nm, or about 75 nm to about 125 nm. In additional embodiments, the mesoporous silica catalyst may have an individual crystal size of about 1 μm to about 100 μm, or about 10 μm to about 40 μm.

Various formulations for the mesoporous silica support, as well as methods of making the formulation, are contemplated. For example, the mesoporous silica catalyst support may be produced via wet impregnation, hydrothermal synthesis, or both. Additionally, the mesoporous silica catalyst support may be characterized by an ordered pore structure. For example, this ordered structure may have a hexagonal array of pores. One suitable embodiment of a mesoporous silica support with a hexagonal pore array may be the Santa Barbara Amorphous (SBA-15) mesoporous silica molecular sieve. Alternatively, another suitable embodiment of a mesoporous silica support is the CARiACT Q-10 (Q-10) spherical catalyst support produced by Fuji Silysia Chemical Ltd.

The catalyst of the metathesis reaction is the impregnated metal oxide of the silica support. The metal oxide may comprise one or oxides of a metal from the Groups 6-10 of the IUPAC Periodic Table. In one or more embodiments, the metal oxide may be an oxide of molybdenum, rhenium, tungsten, or combinations thereof. In a specific embodiment, the metal oxide is tungsten oxide ($WO_3$). It is contemplated that various amounts of metal oxide may be impregnated into the mesoporous silica catalyst support. For example and not by way of limitation, the molar ratio of silica to metal oxide, for example, $WO_3$, is about 5 to about 60, or about 5 to about 15, or about 20 to about 50, or about 20 to about 40, or about 25 to about 35.

In one or more embodiments, the metathesis catalyst may comprise amorphous mesoporous silica foam impregnated with metal oxides. As used in the application, "amorphous mesoporous silica foam" means a silica support with a non-ordered structure and a narrow pore size distribution. This non-ordered structure may be random and thus different than the disclosed hexagonal or cubic structures of conventional silica supports. Specifically, the amorphous mesoporous silica foam has a narrow pore size distribution of at least 3 nm to about 40 nm and a total pore volume of at least 0.700 $cm^3/g$. Without being bound by theory, the present pore size distribution and pore volume are sized to achieve better catalytic activity and reduced blocking of pores by metal oxides, whereas smaller pore volume and pore size metathesis catalysts are susceptible to pore blocking and thereby reduced catalytic activity. Reduced blocking leads to higher dispersion of metal oxide species, such as $WO_3$, on the amorphous mesoporous silica foam. Higher $WO_3$ dispersion leads to higher metathesis activity and thus higher propylene yield.

In one or more embodiments, the pore size distribution of the amorphous mesoporous silica foam impregnated with metal oxides may range from at least 3 nm to about 40 nm, or from about 3 nm to about 20 nm, or from about 4 nm to about 10 nm, or from about 4 nm to about 8 nm, or from about 4 nm to about 6 nm. In further embodiments, the total pore volume may be from at least 0.700 $cm^3/g$ to about 2.5 $cm^3/g$, or from about 0.800 $cm^3/g$ to about 2.5 $cm^3/g$, or from about 0.800 $cm^3/g$ to about 1.5 $cm^3/g$, or from about 0.800 $cm^3/g$ to about 1.25 $cm^3/g$, or from about 0.800 $cm^3/g$ to about 1.0 $cm^3/g$, or from about 0.850 $cm^3/g$ to about 1.0 $cm^3/g$.

Moreover, the amorphous mesoporous silica foam impregnated with metal oxides may have a total acidity from about 0.125 millimole/gram (mmol/g) to about 0.500 mmol/g. Without being bound by theory, if the material exceeds 0.500 mmol/g, other detrimental side reactions may result, such as cracking and hydrogen transfer reactions. In further embodiments, the amorphous mesoporous silica foam impregnated with metal oxides may have a total acidity from about 0.125 mmol/g to about 0.250 mmol/g, or from about 0.125 mmol/g to about 0.150 mmol/g. While various surface areas are contemplated, the metathesis catalyst may, in one or more embodiments, have a surface area of at least about 400 meters²/g (m²/g), or from about 400 m²/g about 800 m²/g, or from about 400 m²/g to about 500 m²/g, or from about 400 m²/g to about 450 m²/g, or from about 425 m²/g to about 450 m²/g.

The catalyst of the metathesis reaction may be the impregnated metal oxide of the silica foam. The metal oxide may comprise one or oxides of a metal from the Periodic Table IUPAC Group Numbers 6-10. In one or more embodiments, the metal oxide may be an oxide of molybdenum, rhenium, tungsten, or combinations thereof. In a specific embodiment, the metal oxide is tungsten oxide ($WO_3$). It is contemplated that various amounts of metal oxide may be impregnated into the amorphous mesoporous silica foam. For example and not by way of limitation, the molar ratio of silica to metal oxide, for example, $WO_3$, is about 1 to about 50, or about 1 to about 40, or about 5 to about 30, or about 5 to about 15. Moreover, the metathesis catalyst may include from about 1 to about 50% by weight, or from about 2 to about 25% by weight, or from about 5 to about 15% by weight metal oxide, for example, $WO_3$.

Additionally, other optional components may be included into the impregnated mesoporous silica foam catalyst. For example, the metathesis catalyst may include a structuring agent. In one embodiment, the structuring agent is a tri-block copolymer structuring agent. In a further embodiment, the tri-block copolymer structuring agent is a poly(ethylene glycol)-block-poly(propylene glycol)-block-poly(ethylene glycol) structure, which may be also called a poloxamer structure. One suitable commercial embodiment of the surfactant tri-block copolymer structuring agent is Pluronic® P123 by BASF Corporation.

Additionally, various silica structures are contemplated for the MFI structured silica catalyst. For example, the MFI structured silica catalyst may include MFI structured aluminosilicate zeolite catalysts or MFI structured silica catalysts free of alumina. As used herein, "free" means less than 0.001% by weight of alumina in the MFI structured silica catalyst. Moreover, it is contemplated that the MFI structured silica catalyst may include other impregnated metal oxides in addition to or as an alternative to alumina. Like the mesoporous silica catalyst, the MFI structured catalysts may have alumina, metal oxides, or both impregnated in the silica support. In addition to or as a substitute for alumina, it is contemplated to include the metal oxides listed prior, specifically, one or more oxides of a metal from Groups 6-10 of the IUPAC Periodic Table, more specifically, metal oxides of molybdenum, rhenium, tungsten, titanium, or combinations thereof.

For the MFI structured aluminosilicate zeolite catalysts, various amounts of alumina are contemplated. In one or more embodiments, the MFI structured aluminosilicate zeolite catalysts may have a molar ratio of silica to alumina of about 5 to about 5000, or about 100 to about 4000, or about 200 to about 3000, or about 1500 to about 2500, or about 1000 to about 2000. Various suitable commercial embodiments of the MFI structured aluminosilicate zeolite catalysts are contemplated, for example, ZSM-5 zeolites such as MFI-280 produced by Zeolyst International or MFI-2000 produced by Saudi Aramco.

Various suitable commercial embodiments are also contemplated for the alumina free MFI structured catalysts. One such example is Silicalite-1 produced by Saudi Aramco.

The MFI structured silica catalyst may include a pore size distribution of from about 1.5 nm to 3 nm, or about 1.5 nm to 2.5 nm. Furthermore, the MFI structured silica catalyst may have a surface area of from about 300 m²/g to about 425 m²/g, or about 340 m²/g to about 410 m²/g. Additionally, the MFI structured silica catalyst may have a total acidity of from about 0.001 mmol/g to about 0.1 mmol/g, or about 0.01 mmol/g to about 0.08 mmol/g. The acidity is maintained at or less than about 0.1 mmol/g in order to reduce production of undesirable byproducts such as aromatics. Increasing acidity may increase the amount of cracking; however, this increased cracking may also lead to less selectivity and increased production of aromatic byproducts, which can lead to catalyst coking and deactivation.

In some cases, MFI structured silica catalyst may be modified with an acidity modifier to adjust the level of acidity in the MFI structured silica catalyst. For example, these acidity modifiers may include rare earth modifiers, phosphorus modifiers, potassium modifiers, or combinations thereof. However, as the present embodiments are focused on reducing the acidity to a level at or below 0.1 mmol/g, the present structured silica catalyst may be free of acidity modifier, such as those selected from rare earth modifiers, phosphorus modifiers, potassium modifiers, or combinations thereof. As used herein, "free of acidity modifiers" means less than less than 0.001% by weight of acidity modifier in the MFI structured silica catalyst.

Further, the MFI structured silica catalyst may have a pore volume of from about 0.1 cm³/g to about 0.3 cm³/g, or about 0.15 cm³/g to about 0.25 cm³/g. Additionally, the MFI structured silica catalyst may have an individual crystal size ranging from about 10 nm to about 40 μm, or from about 15 μm to about 40 μm, or from about 20 μm to about 30 μm. In another embodiment, the MFI structured silica catalyst may have an individual crystal size in a range of from about 1 μm to about 5 μm.

Moreover, various amounts of each catalyst are contemplated for the present dual catalyst system. For example, it is contemplated that the ratio by volume of metathesis catalyst to cracking catalyst may range from about 5:1 to about 1:5, or about 2:1 to about 1:2, or about 1:1.

In operation, a product stream comprising propylene is produced from a butene containing stream via metathesis conversion by contacting the butene stream with the dual catalyst system. The butene stream may comprise 2-butene, and optionally comprises one or more isomers, such as 1-butene, trans-2-butene, and cis-2-butene. The present discussion centers on butene based feed streams; however, it is known that other $C_1$-$C_6$ components may also be present in the feed stream.

The mesoporous silica catalyst may be a metathesis catalyst which facilitates isomerization of 2-butene to 1-butene followed by cross-metathesis of the 2-butene and 1-butene into a metathesis product stream comprising propylene, and other alkenes/alkanes such as pentene. The MFI structured silica catalyst, which is downstream of the metathesis catalyst, is a cracking catalyst which produces propylene from $C_4$ or $C_5$ olefins in the metathesis product stream, and may also yield ethylene.

While the specific catalyst compositions have been described, it should be understood that embodiments of the methods and systems of the present application may incorporate any catalyst that can be utilized to metathesize or crack the reactant compositions described.

EXAMPLES

The various embodiments of methods and systems for the cracking of a light fuel fraction and a heavy fuel fraction by fluidized catalytic cracking will be further clarified by the following examples. The examples are illustrative in nature, and should not be understood to limit the subject matter of the present disclosure.

Example 1

Figure 6:
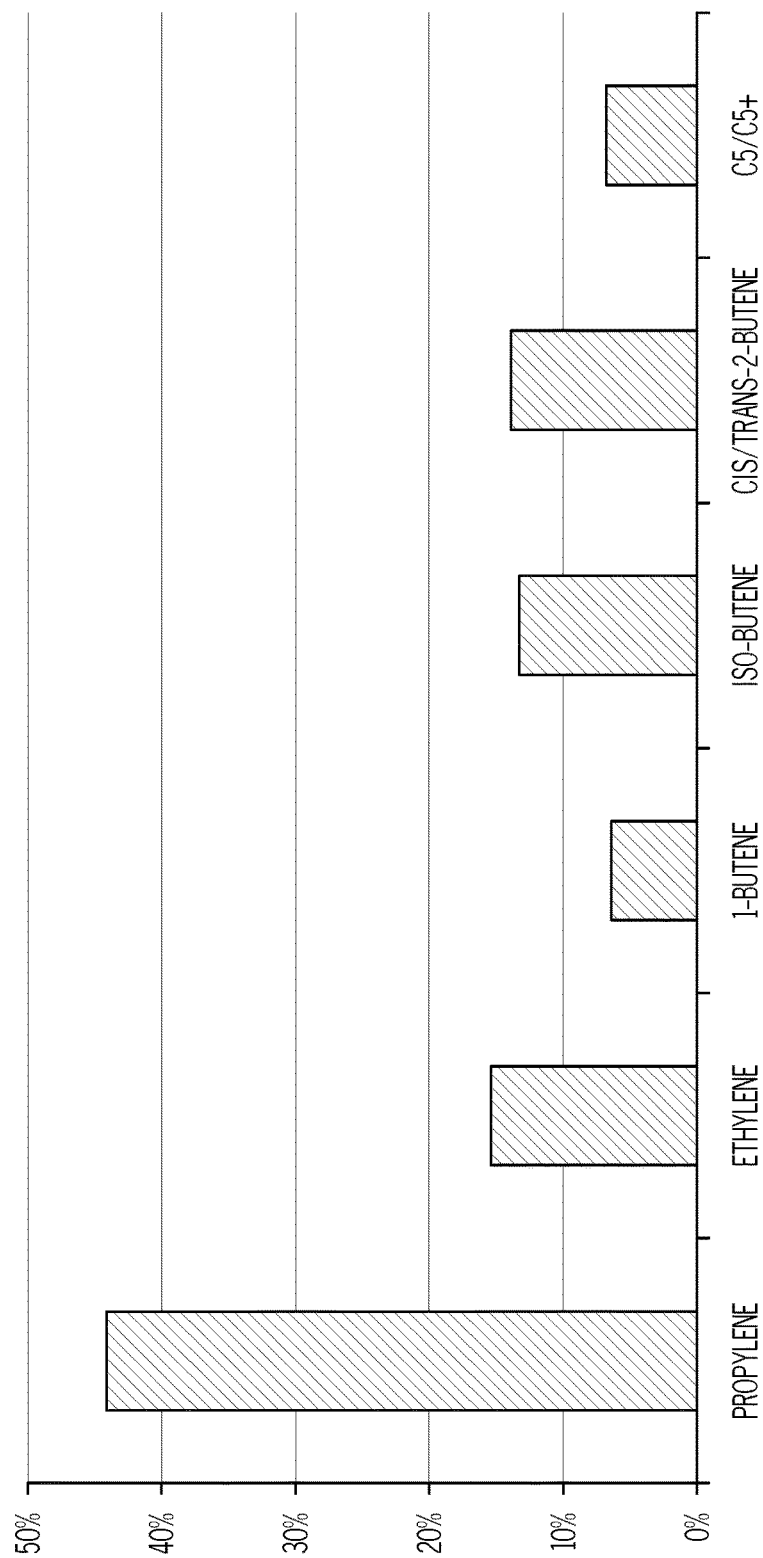
FIG. 6 depicts a bar graph displaying butene conversion (in wt. %) in the system of FIG. 1, according to one or more embodiments described in this disclosure.
Figure 7:
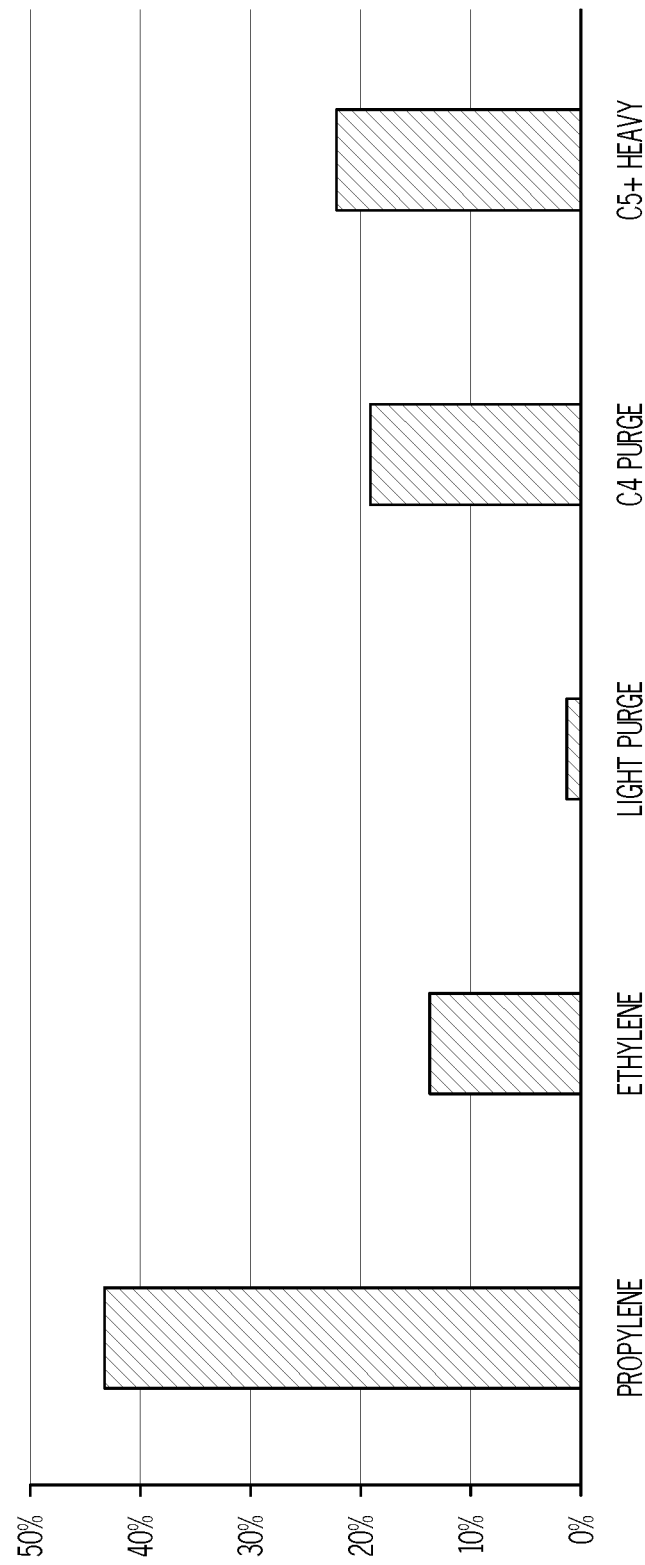
FIG. 7 depicts a bar graph displaying the product distribution (in wt. %) of the system of FIG. 2, according to one or more embodiments described in this disclosure.

The systems of FIG. 1 were computer modeled using Aspen Plus® (commercially available from AspenTech). The subsequent tables (Tables 1-4) depict the stream compositions as well as thermal properties for selected streams. The reaction rates supplied for the simulation were representative of experimental reaction rates for the metathesis catalyst W-SBA-15 and the cracking catalyst MFI-2000, as described in Examples 1, 3, and 6 of co-pending Saudi Aramco U.S. Provisional Patent Application No. 62/188,178 entitled "Dual Catalyst System for Propylene Production". A system inlet stream of 35 wt. % cis-2-butene, 35 wt. % trans-2-butene, and 30 wt. % n-butane was used for the model. The stream numbers of the tables corresponds with the stream or stream segment shown in FIG. 1. Simulations were run for 100% efficiency and 80% efficiency. Data for the simulations is provided on a weight basis and a mole basis for each simulation. Specifically, Table 1 depicts data for a simulation of the system of FIG. 1 with 100% efficiency and shows components on a mass basis. Table 2 depicts data for a simulation of the system of FIG. 1 with 100% efficiency and shows components on a mole basis. Table 3 depicts data for a simulation of the system of FIG. 1 with 80% efficiency and shows components on a mass basis. Table 4 depicts data for a simulation of the system of FIG. 1 with 80% efficiency and shows components on a mole basis. Additionally, FIG. 6 depicts a bar graph displaying the product distribution of the system of FIG. 1 as shown in Table 1 where, on the bar graph, "Propylene" corresponds with the stream of transfer line 207, "Ethylene" corresponds with the stream of transfer line 205, "Light Purge" corresponds with the stream of transfer line 204, and "C4/C5+ Heavy" corresponds with the stream of transfer line 208. FIG. 7 depicts a bar graph displaying the butene conversion products following the metathesis and cracking reactions. The product distribution of FIG. 6 and the butene conversion products of FIG. 7 are based on the Aspen simulations of Table 1.

TABLE 1

FIG. 1 with 100% Efficiency in wt. %

| | Stream Number | | | | | | | | |
|---|---|---|---|---|---|---|---|---|---|
| | 201A | 201D | 203A | 203B | 204 | 205 | 206 | 207 | 208 |
| Mole Flow, kmol/hr | 100 | 100 | 120.2 | 120.2 | 19.7 | 2.2 | 98.3 | 41.3 | 57 |
| Mass Flow, kg/hr | 5670 | 5670 | 5670 | 5670 | 555 | 62 | 5053 | 1738 | 3315 |
| Volume Flow m$^3$/hr | 6750 | 6750 | 8119 | 9.4 | 1.3 | 0.1 | 10.8 | 3.6 | 7.1 |
| Enthalpy, MW | 0.6 | 0.6 | 1.1 | −1 | 0.2 | 0 | −0.9 | 0.1 | −0.9 |
| MW, g/mol | 56.7 | 56.7 | 47.2 | 47.2 | 28.1 | 28.1 | 51.4 | 42.1 | 58.1 |
| Density, kg/m$^3$ | 0.84 | 0.84 | 0.7 | 606.3 | 438 | 438 | 468.4 | 477.4 | 465.7 |
| COMPONENTS, wt. % | | | | | | | | | |
| Ethylene | 0.0 | 0.0 | 10.8 | 10.8 | 99.1 | 99.1 | 0.1 | 0.2 | 0.0 |
| Propylene | 0.0 | 0.0 | 30.9 | 30.9 | 0.9 | 0.9 | 34.6 | 99.5 | 0.5 |
| Propane | 0.0 | 0.0 | 0.0 | 0.0 | 0.0 | 0.0 | 0.0 | 0.0 | 0.0 |
| 1-Butene | 0.0 | 0.0 | 4.4 | 4.4 | 0.0 | 0.0 | 5.0 | 0.1 | 7.5 |
| Isobutene | 0.0 | 0.0 | 9.3 | 9.3 | 0.0 | 0.0 | 10.4 | 0.2 | 15.8 |
| cis-2-butene | 35.0 | 35.0 | 4.4 | 4.4 | 0.0 | 0.0 | 4.9 | 0.0 | 7.5 |
| trans-2-butene | 35.0 | 35.0 | 5.3 | 5.3 | 0.0 | 0.0 | 6.0 | 0.0 | 9.1 |
| n-Butane | 30.0 | 30.0 | 30.0 | 30.0 | 0.0 | 0.0 | 33.7 | 0.0 | 51.3 |
| 1-Pentene | 0.0 | 0.0 | 0.2 | 0.2 | 0.0 | 0.0 | 0.3 | 0.0 | 0.4 |
| cis-2-Pentene | 0.0 | 0.0 | 0.3 | 0.3 | 0.0 | 0.0 | 0.4 | 0.0 | 0.5 |
| trans-2-Pentene | 0.0 | 0.0 | 0.6 | 0.6 | 0.0 | 0.0 | 0.7 | 0.0 | 1.1 |
| 2-Methyl-2-butene | 0.0 | 0.0 | 1.5 | 1.5 | 0.0 | 0.0 | 1.7 | 0.0 | 2.6 |
| 3-Methyl-1-butene | 0.0 | 0.0 | 0.2 | 0.2 | 0.0 | 0.0 | 0.2 | 0.0 | 0.3 |
| 2-Methyl-1-butene | 0.0 | 0.0 | 0.8 | 0.8 | 0.0 | 0.0 | 0.9 | 0.0 | 1.4 |
| Sum of pentenes, | 0.0 | 0.0 | 1.1 | 1.1 | 0.0 | 0.0 | 1.3 | 0.0 | 1.9 |
| pentanes, hexenes, hexanes, and heavier | | | | | | | | | |
| Total wt. % | 100 | 100 | 100 | 100 | 100 | 100 | 100 | 100 | 100 |

TABLE 2

FIG. 1 with 100% Efficiency in mol %

| Stream Number | 201A | 201D | 203A | 203B | 204 | 205 | 206 | 207 | 208 |
|---|---|---|---|---|---|---|---|---|---|
| Mole Flow, kmol/hr | 100 | 100 | 120.2 | 120.2 | 19.7 | 2.2 | 98.3 | 41.3 | 57 |
| Mass Flow, kg/hr | 5670 | 5670 | 5670 | 5670 | 555 | 62 | 5053 | 1738 | 3315 |
| Volume Flow m$^3$/hr | 6750 | 6750 | 8119 | 9.4 | 1.3 | 0.1 | 10.8 | 3.6 | 7.1 |
| Enthalpy, MW | 0.6 | 0.6 | 1.1 | −1 | 0.2 | 0 | −0.9 | 0.1 | −0.9 |
| MW, g/mol | 56.7 | 56.7 | 47.2 | 47.2 | 28.1 | 28.1 | 51.4 | 42.1 | 58.1 |
| Density, kg/m$^3$ | 0.84 | 0.84 | 0.7 | 606.3 | 438 | 438 | 468.4 | 477.4 | 465.7 |

TABLE 2-continued

FIG. 1 with 100% Efficiency in mol %

| Stream Number | 201A | 201D | 203A | 203B | 204 | 205 | 206 | 207 | 208 |
|---|---|---|---|---|---|---|---|---|---|
| COMPONENTS, mol. % | | | | | | | | | |
| Ethylene | 0.0 | 0.0 | 18.2 | 18.2 | 99.4 | 99.4 | 0.1 | 0.3 | 0.0 |
| Propylene | 0.0 | 0.0 | 34.6 | 34.6 | 0.6 | 0.6 | 42.2 | 99.5 | 0.7 |
| Propane | 0.0 | 0.0 | 0.0 | 0.0 | 0.0 | 0.0 | 0.0 | 0.0 | 0.0 |
| 1-Butene | 0.0 | 0.0 | 3.7 | 3.7 | 0.0 | 0.0 | 4.6 | 0.1 | 7.8 |
| Isobutene | 0.0 | 0.0 | 7.8 | 7.8 | 0.0 | 0.0 | 9.5 | 0.2 | 16.3 |
| cis-2-butene | 35.4 | 35.4 | 3.7 | 3.7 | 0.0 | 0.0 | 4.5 | 0.0 | 7.8 |
| trans-2-butene | 35.4 | 35.4 | 4.5 | 4.5 | 0.0 | 0.0 | 5.5 | 0.0 | 9.4 |
| n-Butane | 29.3 | 29.3 | 24.3 | 24.3 | 0.0 | 0.0 | 29.8 | 0.0 | 51.3 |
| 1-Pentene | 0.0 | 0.0 | 0.2 | 0.2 | 0.0 | 0.0 | 0.2 | 0.0 | 0.3 |
| cis-2-Pentene | 0.0 | 0.0 | 0.2 | 0.2 | 0.0 | 0.0 | 0.3 | 0.0 | 0.4 |
| trans-2-Pentene | 0.0 | 0.0 | 0.4 | 0.4 | 0.0 | 0.0 | 0.5 | 0.0 | 0.9 |
| 2-Methyl-2-butene | 0.0 | 0.0 | 1.0 | 1.0 | 0.0 | 0.0 | 1.2 | 0.0 | 2.1 |
| 3-Methyl-1-butene | 0.0 | 0.0 | 0.1 | 0.1 | 0.0 | 0.0 | 0.2 | 0.0 | 0.3 |
| 2-Methyl-1-butene | 0.0 | 0.0 | 0.6 | 0.6 | 0.0 | 0.0 | 0.7 | 0.0 | 1.2 |
| Sum of pentenes, pentanes, hexenes, hexanes, and heavier | 0.0 | 0.0 | 0.6 | 0.6 | 0.0 | 0.0 | 0.7 | 0.0 | 1.3 |
| Total mol. % | 100 | 100 | 100 | 100 | 100 | 100 | 100 | 100 | 100 |

TABLE 3

FIG. 1 with 80% Efficiency in wt. %

| Stream Number | 201A | 201D | 203A | 203B | 204 | 205 | 206 | 207 | 208 |
|---|---|---|---|---|---|---|---|---|---|
| Mole Flow, kmol/hr | 100 | 100 | 116.2 | 116.2 | 15.8 | 1.8 | 98.6 | 33 | 65.6 |
| Mass Flow, kg/hr | 5670 | 5670 | 5670 | 5670 | 444 | 49 | 5176 | 1390 | 3786 |
| Volume Flow m³/hr | 6749.8 | 6749.8 | 7845 | 9.2 | 1 | 0.1 | 11.1 | 2.9 | 8.1 |
| Enthalpy, MW | 0.6 | 0.6 | 1 | −1.1 | 0.1 | 0 | −0.9 | 0 | −1 |
| MW, g/mol | 56.7 | 56.7 | 48.8 | 48.8 | 28.1 | 28.1 | 52.5 | 42.1 | 57.7 |
| Density, kg/m³ | 0.84 | 0.84 | 0.72 | 616.1 | 438 | 438.1 | 467.4 | 477.4 | 467.7 |
| COMPONENTS, wt. % | | | | | | | | | |
| Ethylene | 0.0 | 0.0 | 8.7 | 8.7 | 99.1 | 99.1 | 0.0 | 0.2 | 0.0 |
| Propylene | 0.0 | 0.0 | 24.7 | 24.7 | 0.9 | 0.9 | 27.0 | 99.5 | 0.4 |
| Propane | 0.0 | 0.0 | 0.0 | 0.0 | 0.0 | 0.0 | 0.0 | 0.0 | 0.0 |
| 1-Butene | 0.0 | 0.0 | 3.5 | 3.5 | 0.0 | 0.0 | 3.9 | 0.1 | 5.3 |
| Isobutene | 0.0 | 0.0 | 7.4 | 7.4 | 0.0 | 0.0 | 8.1 | 0.2 | 11.0 |
| cis-2-butene | 35.0 | 35.0 | 10.5 | 10.5 | 0.0 | 0.0 | 11.5 | 0.0 | 15.8 |
| trans-2-butene | 35.0 | 35.0 | 11.3 | 11.3 | 0.0 | 0.0 | 12.3 | 0.0 | 16.9 |
| n-Butane | 30.0 | 30.0 | 30.0 | 30.0 | 0.0 | 0.0 | 32.9 | 0.0 | 44.9 |
| 1-Pentene | 0.0 | 0.0 | 0.2 | 0.2 | 0.0 | 0.0 | 0.2 | 0.0 | 0.3 |
| cis-2-Pentene | 0.0 | 0.0 | 0.3 | 0.3 | 0.0 | 0.0 | 0.3 | 0.0 | 0.4 |
| trans-2-Pentene | 0.0 | 0.0 | 0.5 | 0.5 | 0.0 | 0.0 | 0.5 | 0.0 | 0.7 |
| 2-Methyl-2-butene | 0.0 | 0.0 | 1.2 | 1.2 | 0.0 | 0.0 | 1.3 | 0.0 | 1.8 |
| 3-Methyl-1-butene | 0.0 | 0.0 | 0.2 | 0.2 | 0.0 | 0.0 | 0.2 | 0.0 | 0.2 |
| 2-Methyl-1-butene | 0.0 | 0.0 | 0.7 | 0.7 | 0.0 | 0.0 | 0.7 | 0.0 | 1.0 |
| Sum of pentenes, pentanes, hexenes, hexanes, and heavier | 0.0 | 0.0 | 1.0 | 1.0 | 0.0 | 0.0 | 1.0 | 0.0 | 1.3 |
| Total wt. % | 100 | 100 | 100 | 100 | 100 | 100 | 100 | 100 | 100 |

TABLE 4

FIG. 1 with 80% Efficiency in mol %

| Stream Number | 201A | 201D | 203A | 203B | 204 | 205 | 206 | 207 | 208 |
|---|---|---|---|---|---|---|---|---|---|
| Mole Flow, kmol/hr | 100 | 100 | 116.2 | 116.2 | 15.8 | 1.8 | 98.6 | 33 | 65.6 |
| Mass Flow, kg/hr | 5670 | 5670 | 5670 | 5670 | 444 | 49 | 5176 | 1390 | 3786 |
| Volume Flow m³/hr | 6750 | 6750 | 7845 | 9.2 | 1 | 0.1 | 11.1 | 2.9 | 8.1 |
| Enthalpy, MW | 0.6 | 0.6 | 1 | −1.1 | 0.1 | 0 | −0.9 | 0 | −1 |

TABLE 4-continued

| FIG. 1 with 80% Efficiency in mol % | | | | | | | | | |
|---|---|---|---|---|---|---|---|---|---|
| Stream Number | 201A | 201D | 203A | 203B | 204 | 205 | 206 | 207 | 208 |
| MW, g/mol | 56.7 | 56.7 | 48.8 | 48.8 | 28.1 | 28.1 | 52.5 | 42.1 | 57.7 |
| Density, kg/m$^3$ | 0.84 | 0.84 | 0.72 | 616.1 | 438 | 438.1 | 467.4 | 477.4 | 467.7 |
| COMPONENTS, mol % | | | | | | | | | |
| Ethylene | 0.0 | 0.0 | 15.1 | 15.1 | 99.4 | 99.4 | 0.1 | 0.3 | 0.0 |
| Propylene | 0.0 | 0.0 | 28.7 | 28.7 | 0.6 | 0.6 | 33.7 | 99.5 | 0.5 |
| Propane | 0.0 | 0.0 | 0.0 | 0.0 | 0.0 | 0.0 | 0.0 | 0.0 | 0.0 |
| 1-Butene | 0.0 | 0.0 | 3.1 | 3.1 | 0.0 | 0.0 | 3.6 | 0.1 | 5.4 |
| Isobutene | 0.0 | 0.0 | 6.5 | 6.5 | 0.0 | 0.0 | 7.6 | 0.2 | 11.4 |
| cis-2-butene | 35.4 | 35.4 | 9.2 | 9.2 | 0.0 | 0.0 | 10.8 | 0.0 | 16.2 |
| trans-2-butene | 35.4 | 35.4 | 9.8 | 9.8 | 0.0 | 0.0 | 11.5 | 0.0 | 17.3 |
| n-Butane | 29.3 | 29.3 | 25.2 | 25.2 | 0.0 | 0.0 | 29.7 | 0.0 | 44.6 |
| 1-Pentene | 0.0 | 0.0 | 0.1 | 0.1 | 0.0 | 0.0 | 0.2 | 0.0 | 0.2 |
| cis-2-Pentene | 0.0 | 0.0 | 0.2 | 0.2 | 0.0 | 0.0 | 0.2 | 0.0 | 0.3 |
| trans-2-Pentene | 0.0 | 0.0 | 0.3 | 0.3 | 0.0 | 0.0 | 0.4 | 0.0 | 0.6 |
| 2-Methyl-2-butene | 0.0 | 0.0 | 0.8 | 0.8 | 0.0 | 0.0 | 1.0 | 0.0 | 1.5 |
| 3-Methyl-1-butene | 0.0 | 0.0 | 0.1 | 0.1 | 0.0 | 0.0 | 0.1 | 0.0 | 0.2 |
| 2-Methyl-1-butene | 0.0 | 0.0 | 0.5 | 0.5 | 0.0 | 0.0 | 0.5 | 0.0 | 0.8 |
| Sum of pentenes, pentanes, hexenes, hexanes, and heavier | 0.0 | 0.0 | 0.5 | 0.5 | 0.0 | 0.0 | 0.5 | 0.0 | 1.0 |
| Total mol % | 100 | 100 | 100 | 100 | 100 | 100 | 100 | 100 | 100 |

Example 2

Figure 8:
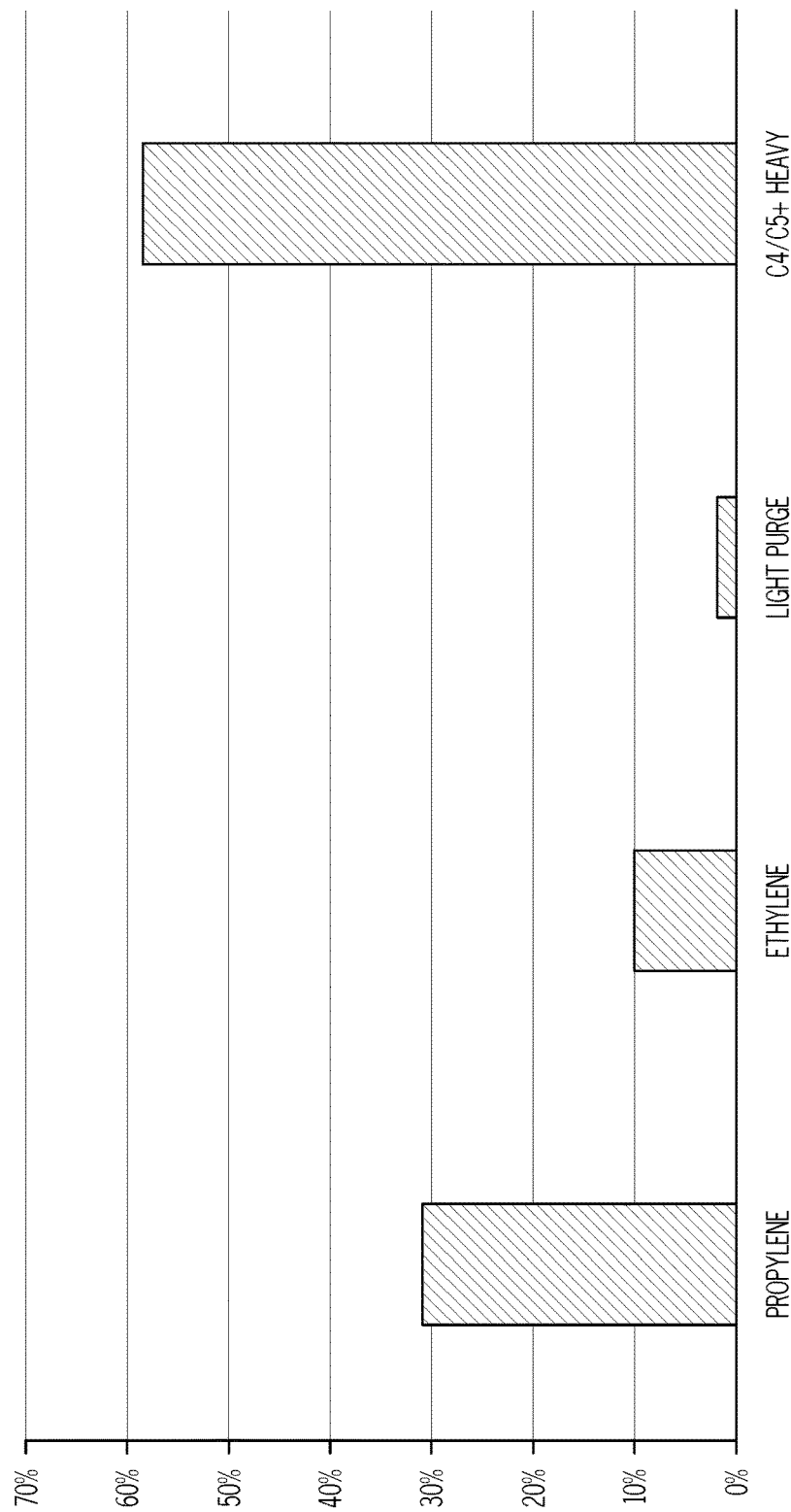
FIG. 8 depicts a bar graph displaying the product distribution (in wt. %) of the system of FIG. 3, according to one or more embodiments described in this disclosure.

The systems of FIG. 2 were also computer modeled using Aspen Plus®. The subsequent tables (Tables 5-8) depict the stream compositions as well as thermal properties for selected streams. The system inlet stream composition and catalyst reaction rates used for the model were the same as those of Example 2. The stream number corresponds with the stream or stream segment shown in FIG. 2. Simulations were run for 100% efficiency and 80% efficiency. Additionally, data is provided on a weight basis and a mole basis for each simulation. Table 5 depicts data for a simulation of the system of FIG. 2 with 100% efficiency and shows components on a mass basis. Table 6 depicts data for a simulation of the system of FIG. 2 with 100% efficiency and shows components on a mole basis. Table 7 depicts data for a simulation of the system of FIG. 2 with 80% efficiency and shows components on a mass basis. Table 8 depicts data for a simulation of the system of FIG. 2 with 80% efficiency and shows components on a mole basis. Additionally, FIG. 8 depicts a bar graph displaying the product distribution of the system of FIG. 2 as shown in Table 5 where, on the bar graph, "Propylene" corresponds with the stream of transfer line 307, "Ethylene" corresponds with the stream of transfer line 305, "Light Purge" corresponds with the stream of transfer line 304, "C4 Purge" corresponds with the stream of transfer line 316, and "C5+Heavy" corresponds with the stream of transfer line 314. The product distribution of FIG. 8 are based on the Aspen simulations of Table 5.

TABLE 5

| FIG. 2 with 100% Efficiency in wt. % | | | | | | | | | | | | |
|---|---|---|---|---|---|---|---|---|---|---|---|---|
| Stream Number | 310 | 301D | 303A | 303B | 304 | 305 | 306 | 307 | 308 | 312 | 316 | 314 |
| Mole Flow, kmol/hr | 100 | 270 | 298 | 298 | 27.9 | 3.1 | 267 | 58 | 209 | 170 | 19 | 20 |
| Mass Flow, kg/hr | 5670 | 15469 | 15469 | 15469 | 785 | 87 | 14597 | 2452 | 12144 | 9799 | 1089 | 1256 |
| Volumn Flow m3/hr | 6750 | 10416 | 14771 | 25 | 1.8 | 0.2 | 32.2 | 5.1 | 26.6 | 20 | 2.2 | 2.5 |
| Enthalpy, MW | 0.6 | −3.5 | −1.7 | −5.5 | 0.2 | 0 | −4.8 | 0.1 | −4.9 | −4.1 | −0.5 | −0.4 |
| MW, g/mol | 56.7 | 57.4 | 51.9 | 51.9 | 28.1 | 28.2 | 54.6 | 42.1 | 58.1 | 57.7 | 57.7 | 61.7 |
| Density, kg/m3 | 0.84 | 1.49 | 1.05 | 618.8 | 438.1 | 438.1 | 453.5 | 477.4 | 456.5 | 490.6 | 490.6 | 496.3 |
| COMPONENTS, wt. % | | | | | | | | | | | | |
| Ethylene | 0.0 | 0.0 | 5.6 | 5.6 | 99.0 | 99.0 | 0.0 | 0.2 | 0.0 | 0.0 | 0.0 | 0.0 |
| Propylene | 0.0 | 0.1 | 16.0 | 16.0 | 1.0 | 1.0 | 16.9 | 99.5 | 0.2 | 0.2 | 0.2 | 0.0 |
| Propane | 0.0 | 0.0 | 0.0 | 0.0 | 0.0 | 0.0 | 0.0 | 0.0 | 0.0 | 0.0 | 0.0 | 0.0 |
| 1-Butene | 0.0 | 2.0 | 2.3 | 2.3 | 0.0 | 0.0 | 2.4 | 0.1 | 2.9 | 3.2 | 3.2 | 0.2 |
| Isobutene | 0.0 | 4.3 | 4.8 | 4.8 | 0.0 | 0.0 | 5.1 | 0.2 | 6.1 | 6.7 | 6.7 | 0.3 |
| cis-2-butene | 35.0 | 14.6 | 2.3 | 2.3 | 0.0 | 0.0 | 2.4 | 0.0 | 2.9 | 2.7 | 2.7 | 4.3 |
| trans-2-butene | 35.0 | 15.1 | 2.8 | 2.8 | 0.0 | 0.0 | 2.9 | 0.0 | 3.5 | 3.6 | 3.6 | 2.6 |
| n-Butane | 30.0 | 63.8 | 63.8 | 63.8 | 0.0 | 0.0 | 67.6 | 0.1 | 81.2 | 83.3 | 83.3 | 63.0 |
| 1-Pentene | 0.0 | 0.0 | 0.1 | 0.1 | 0.0 | 0.0 | 0.1 | 0.0 | 0.2 | 0.0 | 0.0 | 1.4 |
| cis-2-Pentene | 0.0 | 0.0 | 0.2 | 0.2 | 0.0 | 0.0 | 0.2 | 0.0 | 0.2 | 0.0 | 0.0 | 2.0 |
| trans-2-Pentene | 0.0 | 0.0 | 0.3 | 0.3 | 0.0 | 0.0 | 0.3 | 0.0 | 0.4 | 0.0 | 0.0 | 3.9 |
| 2-Methyl-2-butene | 0.0 | 0.0 | 0.8 | 0.8 | 0.0 | 0.0 | 0.8 | 0.0 | 1.0 | 0.0 | 0.0 | 9.5 |
| 3-Methyl-1-butene | 0.0 | 0.0 | 0.1 | 0.1 | 0.0 | 0.0 | 0.1 | 0.0 | 0.1 | 0.0 | 0.0 | 0.9 |

TABLE 5-continued

FIG. 2 with 100% Efficiency in wt. %

| Stream Number | 310 | 301D | 303A | 303B | 304 | 305 | 306 | 307 | 308 | 312 | 316 | 314 |
|---|---|---|---|---|---|---|---|---|---|---|---|---|
| 2-Methyl-1-butene | 0.0 | 0.0 | 0.4 | 0.4 | 0.0 | 0.0 | 0.5 | 0.0 | 0.5 | 0.0 | 0.0 | 4.9 |
| Sum of pentenes, | 0.0 | 0.0 | 0.5 | 0.5 | 0.0 | 0.0 | 0.5 | 0.0 | 0.7 | 0.0 | 0.0 | 7.1 |
| pentanes, hexenes, hexanes, and heavier | | | | | | | | | | | | |
| Total wt. % | 100 | 100 | 100 | 100 | 100 | 100 | 100 | 100 | 100 | 100 | 100 | 100 |

TABLE 6

FIG. 2 with 100% Efficiency in mol %

| Stream Number | 310 | 301D | 303A | 303B | 304 | 305 | 306 | 307 | 308 | 312 | 316 | 314 |
|---|---|---|---|---|---|---|---|---|---|---|---|---|
| Mole Flow, kmol/hr | 100 | 270 | 298 | 298 | 27.9 | 3.1 | 267 | 58 | 209 | 170 | 19 | 20 |
| Mass Flow, kg/hr | 5670 | 15469 | 15469 | 15469 | 785 | 87 | 14597 | 2452 | 12144 | 9799 | 1089 | 1256 |
| Volumn Flow m3/hr | 6750 | 10416 | 14771 | 25 | 1.8 | 0.2 | 32.2 | 5.1 | 26.6 | 20 | 2.2 | 2.5 |
| Enthalpy, MW | 0.6 | −3.5 | −1.7 | −5.5 | 0.2 | 0 | −4.8 | 0.1 | −4.9 | −4.1 | −0.5 | −0.4 |
| MW, g/mol | 56.7 | 57.4 | 51.9 | 51.9 | 28.1 | 28.2 | 54.6 | 42.1 | 58.1 | 57.7 | 57.7 | 61.7 |
| Density, kg/m3 | 0.84 | 1.49 | 1.05 | 618.8 | 438.1 | 438.1 | 453.5 | 477.4 | 456.5 | 490.6 | 490.6 | 496.3 |
| COMPONENTS, mol % | | | | | | | | | | | | |
| Ethylene | 0.0 | 0.0 | 10.4 | 10.4 | 99.3 | 99.3 | 0.1 | 0.3 | 0.0 | 0.0 | 0.0 | 0.0 |
| Propylene | 0.0 | 0.2 | 19.7 | 19.7 | 0.7 | 0.7 | 21.9 | 99.5 | 0.3 | 0.3 | 0.3 | 0.0 |
| Propane | 0.0 | 0.0 | 0.0 | 0.0 | 0.0 | 0.0 | 0.0 | 0.0 | 0.0 | 0.0 | 0.0 | 0.0 |
| 1-Butene | 0.0 | 2.1 | 2.1 | 2.1 | 0.0 | 0.0 | 2.4 | 0.0 | 3.0 | 3.3 | 3.3 | 0.2 |
| Isobutene | 0.0 | 4.4 | 4.4 | 4.4 | 0.0 | 0.0 | 5.0 | 0.1 | 6.3 | 6.9 | 6.9 | 0.4 |
| cis-2-butene | 35.4 | 14.9 | 2.1 | 2.1 | 0.0 | 0.0 | 2.4 | 0.0 | 3.0 | 2.8 | 2.8 | 4.8 |
| trans-2-butene | 35.4 | 15.5 | 2.6 | 2.6 | 0.0 | 0.0 | 2.8 | 0.0 | 3.6 | 3.7 | 3.7 | 2.8 |
| n-Butane | 29.3 | 62.9 | 56.9 | 56.9 | 0.0 | 0.0 | 63.5 | 0.1 | 81.2 | 82.8 | 82.8 | 66.9 |
| 1-Pentene | 0.0 | 0.0 | 0.1 | 0.1 | 0.0 | 0.0 | 0.1 | 0.0 | 0.1 | 0.0 | 0.0 | 1.2 |
| cis-2-Pentene | 0.0 | 0.0 | 0.1 | 0.1 | 0.0 | 0.0 | 0.1 | 0.0 | 0.2 | 0.0 | 0.0 | 1.7 |
| trans-2-Pentene | 0.0 | 0.0 | 0.2 | 0.2 | 0.0 | 0.0 | 0.3 | 0.0 | 0.3 | 0.0 | 0.0 | 3.4 |
| 2-Methyl-2-butene | 0.0 | 0.0 | 0.6 | 0.6 | 0.0 | 0.0 | 0.6 | 0.0 | 0.8 | 0.0 | 0.0 | 8.4 |
| 3-Methyl-1-butene | 0.0 | 0.0 | 0.1 | 0.1 | 0.0 | 0.0 | 0.1 | 0.0 | 0.1 | 0.0 | 0.0 | 0.8 |
| 2-Methyl-1-butene | 0.0 | 0.0 | 0.3 | 0.3 | 0.0 | 0.0 | 0.4 | 0.0 | 0.5 | 0.0 | 0.0 | 4.3 |
| Sum of pentenes, | 0.0 | 0.0 | 0.3 | 0.3 | 0.0 | 0.0 | 0.5 | 0.0 | 0.5 | 0.0 | 0.0 | 5.0 |
| pentanes, hexenes, hexanes, and heavier | | | | | | | | | | | | |
| Total mol % | 100 | 100 | 100 | 100 | 100 | 100 | 100 | 100 | 100 | 100 | 100 | 100 |

TABLE 7

FIG. 2 with 80% Efficiency in wt. %

| Stream Number | 310 | 301D | 303A | 303B | 304 | 305 | 306 | 307 | 308 | 312 | 316 | 314 |
|---|---|---|---|---|---|---|---|---|---|---|---|---|
| Mole Flow, kmol/hr | 100 | 318 | 345 | 345 | 26.5 | 2.9 | 316 | 55 | 260 | 218 | 24 | 18 |
| Mass Flow, kg/hr | 5670 | 18231 | 18231 | 18231 | 746 | 83 | 17403 | 2334 | 15069 | 12562 | 1396 | 1112 |
| Volumn Flow m3/hr | 6750 | 11290 | 15751 | 29.2 | 1.7 | 0.2 | 38.5 | 4.9 | 32.9 | 25.5 | 2.8 | 2.2 |
| Enthalpy, MW | 0.6 | −4.4 | −2.7 | −6.6 | 0.2 | 0 | −5.6 | 0.1 | −5.7 | −5 | −0.6 | −0.4 |
| MW, g/mol | 56.7 | 57.4 | 52.9 | 52.9 | 28.1 | 28.2 | 55.2 | 42.1 | 57.9 | 57.7 | 57.7 | 61.8 |
| Density, kg/m3 | 0.84 | 1.61 | 1.16 | 623.6 | 438.1 | 438.1 | 452 | 477.4 | 457.7 | 492 | 492 | 499.4 |
| COMPONENTS, wt. % | | | | | | | | | | | | |
| Ethylene | 0.0 | 0.0 | 4.5 | 4.5 | 99.0 | 99.0 | 0.0 | 0.2 | 0.0 | 0.0 | 0.0 | 0.0 |
| Propylene | 0.0 | 0.1 | 12.9 | 12.9 | 1.0 | 1.0 | 13.5 | 99.5 | 0.2 | 0.2 | 0.2 | 0.0 |
| Propane | 0.0 | 0.0 | 0.0 | 0.0 | 0.0 | 0.0 | 0.0 | 0.0 | 0.0 | 0.0 | 0.0 | 0.0 |
| 1-Butene | 0.0 | 2.0 | 2.2 | 2.2 | 0.0 | 0.0 | 2.4 | 0.1 | 2.7 | 2.9 | 2.9 | 0.1 |
| Isobutene | 0.0 | 4.2 | 4.7 | 4.7 | 0.0 | 0.0 | 4.9 | 0.2 | 5.7 | 6.1 | 6.1 | 0.2 |
| cis-2-butene | 35.0 | 14.7 | 4.8 | 4.8 | 0.0 | 0.0 | 5.0 | 0.0 | 5.8 | 5.5 | 5.5 | 9.3 |
| trans-2-butene | 35.0 | 15.4 | 5.3 | 5.3 | 0.0 | 0.0 | 5.6 | 0.0 | 6.4 | 6.6 | 6.6 | 4.3 |
| n-Butane | 30.0 | 63.5 | 63.5 | 63.5 | 0.0 | 0.0 | 66.5 | 0.1 | 76.8 | 78.6 | 78.6 | 54.1 |
| 1-Pentene | 0.0 | 0.0 | 0.1 | 0.1 | 0.0 | 0.0 | 0.1 | 0.0 | 0.1 | 0.0 | 0.0 | 1.5 |
| cis-2-Pentene | 0.0 | 0.0 | 0.1 | 0.1 | 0.0 | 0.0 | 0.1 | 0.0 | 0.2 | 0.0 | 0.0 | 2.1 |
| trans-2-Pentene | 0.0 | 0.0 | 0.3 | 0.3 | 0.0 | 0.0 | 0.3 | 0.0 | 0.3 | 0.0 | 0.0 | 4.2 |
| 2-Methyl-2-butene | 0.0 | 0.0 | 0.6 | 0.6 | 0.0 | 0.0 | 0.7 | 0.0 | 0.8 | 0.0 | 0.0 | 10.3 |

TABLE 7-continued

FIG. 2 with 80% Efficiency in wt. %

| Stream Number | 310 | 301D | 303A | 303B | 304 | 305 | 306 | 307 | 308 | 312 | 316 | 314 |
|---|---|---|---|---|---|---|---|---|---|---|---|---|
| 3-Methyl-1-butene | 0.0 | 0.0 | 0.1 | 0.1 | 0.0 | 0.0 | 0.1 | 0.0 | 0.1 | 0.0 | 0.0 | 1.0 |
| 2-Methyl-1-butene | 0.0 | 0.0 | 0.4 | 0.4 | 0.0 | 0.0 | 0.4 | 0.0 | 0.4 | 0.0 | 0.0 | 5.3 |
| Sum of pentenes, pentanes, hexenes, hexanes, and heavier | 0.0 | 0.0 | 0.5 | 0.5 | 0.0 | 0.0 | 0.5 | 0.0 | 0.5 | 0.0 | 0.0 | 7.5 |
| Total wt. % | 100 | 100 | 100 | 100 | 100 | 100 | 100 | 100 | 100 | 100 | 100 | 100 |

TABLE 8

FIG. 2 with 80% Efficiency in mol %

| Stream Number | 310 | 301D | 303A | 303B | 304 | 305 | 306 | 307 | 308 | 312 | 316 | 314 |
|---|---|---|---|---|---|---|---|---|---|---|---|---|
| Mole Flow, kmol/hr | 100 | 318 | 345 | 345 | 26 | 3 | 316 | 55 | 260 | 218 | 24 | 18 |
| Mass Flow, kg/hr | 5670 | 18231 | 18231 | 18231 | 746 | 83 | 17403 | 2334 | 15069 | 12562 | 1396 | 1112 |
| Volumn Flow m3/hr | 6750 | 11290 | 15751 | 29.2 | 1.7 | 0.2 | 38.5 | 4.9 | 32.9 | 25.5 | 2.8 | 2.2 |
| Enthalpy, MW | 0.6 | −4.4 | −2.7 | −6.6 | 0.2 | 0 | −5.6 | 0.1 | −5.7 | −5 | −0.6 | −0.4 |
| MW, g/mol | 56.7 | 57.4 | 52.9 | 52.9 | 28.1 | 28.2 | 55.2 | 42.1 | 57.9 | 57.7 | 57.7 | 61.8 |
| Density, kg/m3 | 0.84 | 1.61 | 1.16 | 623.6 | 438.1 | 438.1 | 452 | 477.4 | 457.7 | 492 | 492 | 499.4 |
| COMPONENTS, mol % | | | | | | | | | | | | |
| Ethylene | 0.0 | 0.0 | 8.5 | 8.5 | 99.3 | 99.3 | 0.0 | 0.3 | 0.0 | 0.0 | 0.0 | 0.0 |
| Propylene | 0.0 | 0.2 | 16.2 | 16.2 | 0.7 | 0.7 | 17.7 | 99.5 | 0.2 | 0.2 | 0.2 | 0.0 |
| Propane | 0.0 | 0.0 | 0.0 | 0.0 | 0.0 | 0.0 | 0.0 | 0.0 | 0.0 | 0.0 | 0.0 | 0.0 |
| 1-Butene | 0.0 | 2.1 | 2.1 | 2.1 | 0.0 | 0.0 | 2.3 | 0.0 | 2.8 | 3.0 | 3.0 | 0.1 |
| Isobutene | 0.0 | 4.3 | 4.4 | 4.4 | 0.0 | 0.0 | 4.9 | 0.1 | 5.9 | 6.3 | 6.3 | 0.2 |
| cis-2-butene | 35.4 | 15.0 | 4.5 | 4.5 | 0.0 | 0.0 | 4.9 | 0.0 | 6.0 | 5.6 | 5.6 | 10.3 |
| trans-2-butene | 35.4 | 15.8 | 5.0 | 5.0 | 0.0 | 0.0 | 5.5 | 0.0 | 6.6 | 6.8 | 6.8 | 4.7 |
| n-Butane | 29.3 | 62.7 | 57.7 | 57.7 | 0.0 | 0.0 | 63.1 | 0.1 | 76.6 | 78.0 | 78.0 | 57.6 |
| 1-Pentene | 0.0 | 0.0 | 0.1 | 0.1 | 0.0 | 0.0 | 0.1 | 0.0 | 0.1 | 0.0 | 0.0 | 1.4 |
| cis-2-Pentene | 0.0 | 0.0 | 0.1 | 0.1 | 0.0 | 0.0 | 0.1 | 0.0 | 0.1 | 0.0 | 0.0 | 1.9 |
| trans-2-Pentene | 0.0 | 0.0 | 0.2 | 0.2 | 0.0 | 0.0 | 0.2 | 0.0 | 0.3 | 0.0 | 0.0 | 3.7 |
| 2-Methyl-2-butene | 0.0 | 0.0 | 0.5 | 0.5 | 0.0 | 0.0 | 0.5 | 0.0 | 0.6 | 0.0 | 0.0 | 9.0 |
| 3-Methyl-1-butene | 0.0 | 0.0 | 0.1 | 0.1 | 0.0 | 0.0 | 0.1 | 0.0 | 0.1 | 0.0 | 0.0 | 0.8 |
| 2-Methyl-1-butene | 0.0 | 0.0 | 0.3 | 0.3 | 0.0 | 0.0 | 0.3 | 0.0 | 0.4 | 0.0 | 0.0 | 4.7 |
| Sum of pentenes, pentanes, hexenes, hexanes, and heavier | 0.0 | 0.0 | 0.3 | 0.3 | 0.0 | 0.0 | 0.3 | 0.0 | 0.5 | 0.0 | 0.0 | 5.7 |
| Total mol % | 100 | 100 | 100 | 100 | 100 | 100 | 100 | 100 | 100 | 100 | 100 | 100 |

Example 3

Figure 9:
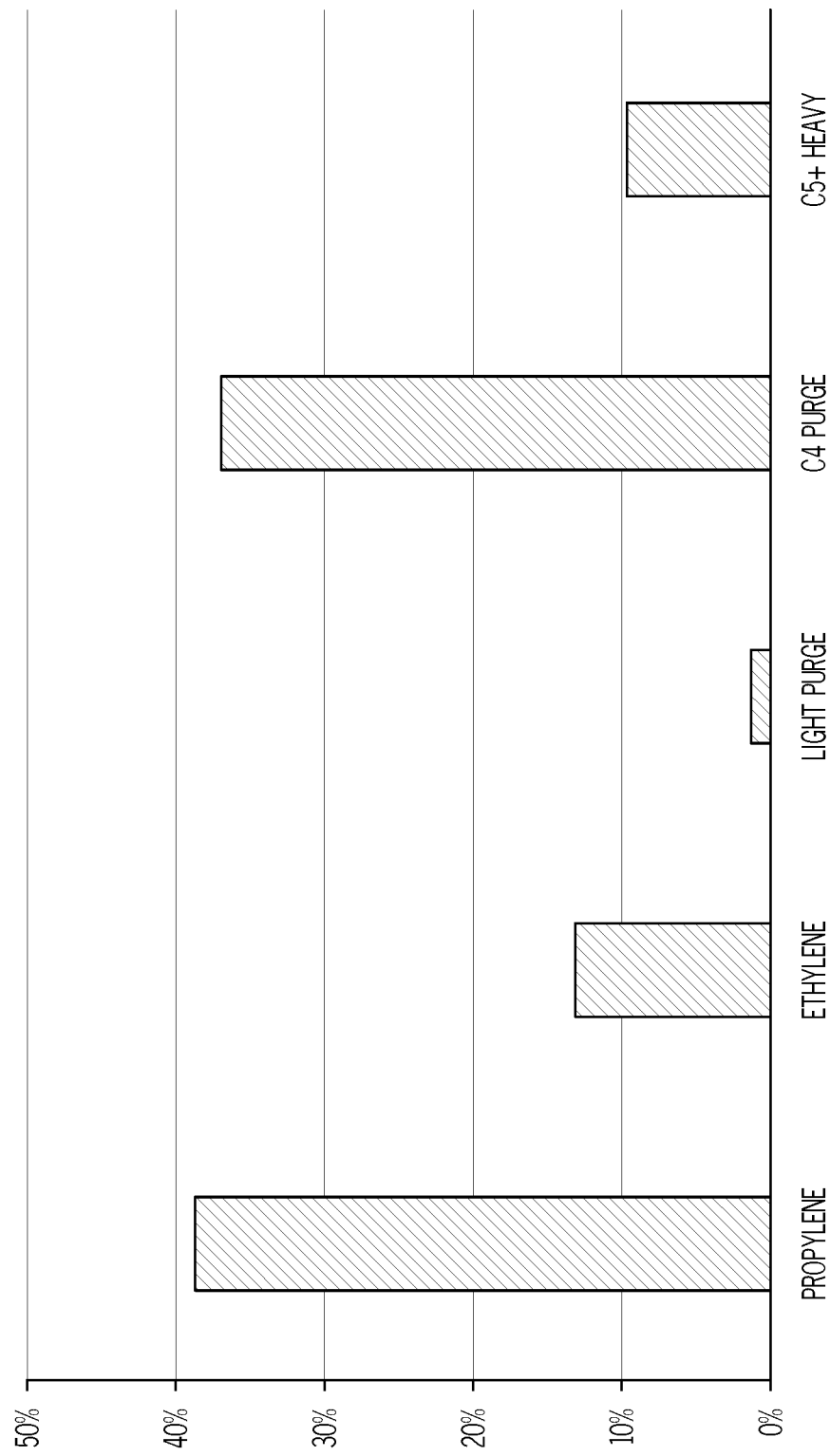
FIG. 9 depicts a bar graph displaying the product distribution (in wt. %) of the system of FIG. 4, according to one or more embodiments described in this disclosure.

The systems of FIG. 3 were also computer modeled using Aspen Plus®. The subsequent tables (Tables 9-12) depict the stream compositions as well as thermal properties for selected streams. The system inlet stream composition and catalyst reaction rates used for the model were the same as those of Example 1. The stream number corresponds with the stream or stream segment shown in FIG. 3. Simulations were run for 100% efficiency and 80% efficiency. Additionally, data is provided on a weight basis and a mole basis for each simulation. Table 9 depicts data for a simulation of the system of FIG. 3 with 100% efficiency and shows components on a mass basis. Table 10 depicts data for a simulation of the system of FIG. 3 with 100% efficiency and shows components on a mole basis. Table 11 depicts data for a simulation of the system of FIG. 3 with 80% efficiency and shows components on a mass basis. Table 12 depicts data for a simulation of the system of FIG. 3 with 80% efficiency and shows components on a mole basis. Additionally, FIG. 9 depicts a bar graph displaying the product distribution of the system of FIG. 3 as shown in Table 9 where, on the bar graph, "Propylene" corresponds with the stream of transfer line 407, "Ethylene" corresponds with the stream of transfer line 405, "Light Purge" corresponds with the stream of transfer line 404, and "C4/C5+Heavy" corresponds with the stream of transfer line 408. The product distribution of FIG. 9 are based on the Aspen simulations of Table 9.

TABLE 9

FIG. 3 with 100% Efficiency in wt. %

| Stream Number | 401A | 401D | 403A | 403B | 404 | 405 | 406 | 407 | 408 |
|---|---|---|---|---|---|---|---|---|---|
| Mole Flow, kmol/hr | 100 | 100 | 120.2 | 120.2 | 19.7 | 2.2 | 98.3 | 41.3 | 57 |
| Mass Flow, kg/hr | 5670 | 5670 | 5670 | 5670 | 555 | 62 | 5053 | 1738 | 3315 |
| Volume Flow m³/hr | 6750 | 6750 | 8119 | 9.4 | 1.3 | 0.1 | 10.8 | 3.6 | 7.1 |

TABLE 9-continued

FIG. 3 with 100% Efficiency in wt. %

| Stream Number | 401A | 401D | 403A | 403B | 404 | 405 | 406 | 407 | 408 |
|---|---|---|---|---|---|---|---|---|---|
| Enthalpy, MW | 0.6 | 0.6 | 1.1 | −1 | 0.2 | 0 | −0.9 | 0.1 | −0.9 |
| MW, g/mol | 56.7 | 56.7 | 47.2 | 47.2 | 28.1 | 28.1 | 51.4 | 42.1 | 58.1 |
| Density, kg/m$^3$ | 0.84 | 0.84 | 0.7 | 606.3 | 438 | 438 | 468.4 | 477.4 | 465.7 |
| COMPONENTS, wt. % | | | | | | | | | |
| Ethylene | 0.0 | 0.0 | 10.8 | 10.8 | 99.1 | 99.1 | 0.1 | 0.2 | 0.0 |
| Propylene | 0.0 | 0.0 | 30.9 | 30.9 | 0.9 | 0.9 | 34.6 | 99.5 | 0.5 |
| Propane | 0.0 | 0.0 | 0.0 | 0.0 | 0.0 | 0.0 | 0.0 | 0.0 | 0.0 |
| 1-Butene | 0.0 | 0.0 | 4.4 | 4.4 | 0.0 | 0.0 | 5.0 | 0.1 | 7.5 |
| Isobutene | 0.0 | 0.0 | 9.3 | 9.3 | 0.0 | 0.0 | 10.4 | 0.2 | 15.8 |
| cis-2-butene | 35.0 | 35.0 | 4.4 | 4.4 | 0.0 | 0.0 | 4.9 | 0.0 | 7.5 |
| trans-2-butene | 35.0 | 35.0 | 5.3 | 5.3 | 0.0 | 0.0 | 6.0 | 0.0 | 9.1 |
| n-Butane | 30.0 | 30.0 | 30.0 | 30.0 | 0.0 | 0.0 | 33.7 | 0.0 | 51.3 |
| 1-Pentene | 0.0 | 0.0 | 0.2 | 0.2 | 0.0 | 0.0 | 0.3 | 0.0 | 0.4 |
| cis-2-Pentene | 0.0 | 0.0 | 0.3 | 0.3 | 0.0 | 0.0 | 0.4 | 0.0 | 0.5 |
| trans-2-Pentene | 0.0 | 0.0 | 0.6 | 0.6 | 0.0 | 0.0 | 0.7 | 0.0 | 1.1 |
| 2-Methyl-2-butene | 0.0 | 0.0 | 1.5 | 1.5 | 0.0 | 0.0 | 1.7 | 0.0 | 2.6 |
| 3-Methyl-1-butene | 0.0 | 0.0 | 0.2 | 0.2 | 0.0 | 0.0 | 0.2 | 0.0 | 0.3 |
| 2-Methyl-1-butene | 0.0 | 0.0 | 0.8 | 0.8 | 0.0 | 0.0 | 0.9 | 0.0 | 1.4 |
| Sum of pentenes, | 0.0 | 0.0 | 1.1 | 1.1 | 0.0 | 0.0 | 1.3 | 0.0 | 1.9 |
| pentanes, hexenes, hexanes, and heavier | | | | | | | | | |
| Total wt. % | 100 | 100 | 100 | 100 | 100 | 100 | 100 | 100 | 100 |

TABLE 10

FIG. 3 with 100% Efficiency in mol %

| Stream Number | 401A | 401D | 403A | 403B | 404 | 405 | 406 | 407 | 408 |
|---|---|---|---|---|---|---|---|---|---|
| Mole Flow, kmol/hr | 100 | 100 | 120.2 | 120.2 | 19.7 | 2.2 | 98.3 | 41.3 | 57 |
| Mass Flow, kg/hr | 5670 | 5670 | 5670 | 5670 | 555 | 62 | 5053 | 1738 | 3315 |
| Volume Flow m$^3$/hr | 6750 | 6750 | 8119 | 9.4 | 1.3 | 0.1 | 10.8 | 3.6 | 7.1 |
| Enthalpy, MW | 0.6 | 0.6 | 1.1 | −1 | 0.2 | 0 | −0.9 | 0.1 | −0.9 |
| MW, g/mol | 56.7 | 56.7 | 47.2 | 47.2 | 28.1 | 28.1 | 51.4 | 42.1 | 58.1 |
| Density, kg/m$^3$ | 0.84 | 0.84 | 0.7 | 606.3 | 438 | 438 | 468.4 | 477.4 | 465.7 |
| COMPONENTS, mol % | | | | | | | | | |
| Ethylene | 0.0 | 0.0 | 18.2 | 18.2 | 99.4 | 99.4 | 0.1 | 0.3 | 0.0 |
| Propylene | 0.0 | 0.0 | 34.6 | 34.6 | 0.6 | 0.6 | 42.2 | 99.5 | 0.7 |
| Propane | 0.0 | 0.0 | 0.0 | 0.0 | 0.0 | 0.0 | 0.0 | 0.0 | 0.0 |
| 1-Butene | 0.0 | 0.0 | 3.7 | 3.7 | 0.0 | 0.0 | 4.6 | 0.1 | 7.8 |
| Isobutene | 0.0 | 0.0 | 7.8 | 7.8 | 0.0 | 0.0 | 9.5 | 0.2 | 16.3 |
| cis-2-butene | 35.4 | 35.4 | 3.7 | 3.7 | 0.0 | 0.0 | 4.5 | 0.0 | 7.8 |
| trans-2-butene | 35.4 | 35.4 | 4.5 | 4.5 | 0.0 | 0.0 | 5.5 | 0.0 | 9.4 |
| n-Butane | 29.3 | 29.3 | 24.3 | 24.3 | 0.0 | 0.0 | 29.8 | 0.0 | 51.3 |
| 1-Pentene | 0.0 | 0.0 | 0.2 | 0.2 | 0.0 | 0.0 | 0.2 | 0.0 | 0.3 |
| cis-2-Pentene | 0.0 | 0.0 | 0.2 | 0.2 | 0.0 | 0.0 | 0.3 | 0.0 | 0.4 |
| trans-2-Pentene | 0.0 | 0.0 | 0.4 | 0.4 | 0.0 | 0.0 | 0.5 | 0.0 | 0.9 |
| 2-Methyl-2-butene | 0.0 | 0.0 | 1.0 | 1.0 | 0.0 | 0.0 | 1.2 | 0.0 | 2.1 |
| 3-Methyl-1-butene | 0.0 | 0.0 | 0.1 | 0.1 | 0.0 | 0.0 | 0.2 | 0.0 | 0.3 |
| 2-Methyl-1-butene | 0.0 | 0.0 | 0.6 | 0.6 | 0.0 | 0.0 | 0.7 | 0.0 | 1.2 |
| Sum of pentenes, | 0.0 | 0.0 | 0.6 | 0.6 | 0.0 | 0.0 | 0.7 | 0.0 | 1.3 |
| pentanes, hexenes, hexanes, and heavier | | | | | | | | | |
| Total mol % | 100 | 100 | 100 | 100 | 100 | 100 | 100 | 100 | 100 |

TABLE 11

FIG. 3 with 80% Efficiency in wt. %

| Stream Number | 401A | 401D | 403A | 403B | 404 | 405 | 406 | 407 | 408 |
|---|---|---|---|---|---|---|---|---|---|
| Mole Flow, kmol/hr | 100 | 100 | 120.2 | 120.2 | 19.7 | 2.2 | 98.3 | 41.3 | 57 |
| Mass Flow, kg/hr | 5670 | 5670 | 5670 | 5670 | 555 | 62 | 5053 | 1738 | 3315 |
| Volume Flow m$^3$/hr | 6750 | 6750 | 8119 | 9.4 | 1.3 | 0.1 | 10.8 | 3.6 | 7.1 |
| Enthalpy, MW | 0.6 | 0.6 | 1.1 | −1 | 0.2 | 0 | −0.9 | 0.1 | −0.9 |
| MW, g/mol | 56.7 | 56.7 | 47.2 | 47.2 | 28.1 | 28.1 | 51.4 | 42.1 | 58.1 |
| Density, kg/m$^3$ | 0.84 | 0.84 | 0.7 | 606.3 | 438 | 438 | 468.4 | 477.4 | 465.7 |
| COMPONENTS, mol % | | | | | | | | | |
| Ethylene | 0.0 | 0.0 | 18.2 | 18.2 | 99.4 | 99.4 | 0.1 | 0.3 | 0.0 |
| Propylene | 0.0 | 0.0 | 34.6 | 34.6 | 0.6 | 0.6 | 42.2 | 99.5 | 0.7 |
| Propane | 0.0 | 0.0 | 0.0 | 0.0 | 0.0 | 0.0 | 0.0 | 0.0 | 0.0 |
| 1-Butene | 0.0 | 0.0 | 3.7 | 3.7 | 0.0 | 0.0 | 4.6 | 0.1 | 7.8 |
| Isobutene | 0.0 | 0.0 | 7.8 | 7.8 | 0.0 | 0.0 | 9.5 | 0.2 | 16.3 |
| cis-2-butene | 35.4 | 35.4 | 3.7 | 3.7 | 0.0 | 0.0 | 4.5 | 0.0 | 7.8 |
| trans-2-butene | 35.4 | 35.4 | 4.5 | 4.5 | 0.0 | 0.0 | 5.5 | 0.0 | 9.4 |
| n-Butane | 29.3 | 29.3 | 24.3 | 24.3 | 0.0 | 0.0 | 29.8 | 0.0 | 51.3 |
| 1-Pentene | 0.0 | 0.0 | 0.2 | 0.2 | 0.0 | 0.0 | 0.2 | 0.0 | 0.3 |
| cis-2-Pentene | 0.0 | 0.0 | 0.2 | 0.2 | 0.0 | 0.0 | 0.3 | 0.0 | 0.4 |
| trans-2-Pentene | 0.0 | 0.0 | 0.4 | 0.4 | 0.0 | 0.0 | 0.5 | 0.0 | 0.9 |
| 2-Methyl-2-butene | 0.0 | 0.0 | 1.0 | 1.0 | 0.0 | 0.0 | 1.2 | 0.0 | 2.1 |
| 3-Methyl-1-butene | 0.0 | 0.0 | 0.1 | 0.1 | 0.0 | 0.0 | 0.2 | 0.0 | 0.3 |
| 2-Methyl-1-butene | 0.0 | 0.0 | 0.6 | 0.6 | 0.0 | 0.0 | 0.7 | 0.0 | 1.2 |
| Sum of pentenes, pentanes, hexenes, hexanes, and heavier | 0.0 | 0.0 | 0.6 | 0.6 | 0.0 | 0.0 | 0.7 | 0.0 | 1.3 |
| Total mol % | 100 | 100 | 100 | 100 | 100 | 100 | 100 | 100 | 100 |

TABLE 12

FIG. 3 with 80% Efficiency in mol %

| Stream Number | 401A | 401D | 403A | 403B | 404 | 405 | 406 | 407 | 408 |
|---|---|---|---|---|---|---|---|---|---|
| Mole Flow, kmol/hr | 100 | 100 | 116.2 | 116.2 | 15.8 | 1.8 | 98.6 | 33 | 65.6 |
| Mass Flow, kg/hr | 5670 | 5670 | 5670 | 5670 | 444 | 49 | 5176 | 1390 | 3786 |
| Volume Flow m$^3$/hr | 6750 | 6750 | 7845 | 9.2 | 1 | 0.1 | 11.1 | 2.9 | 8.1 |
| Enthalpy, MW | 0.6 | 0.6 | 1 | −1.1 | 0.1 | 0 | −0.9 | 0 | −1 |
| MW, g/mol | 56.7 | 56.7 | 48.8 | 48.8 | 28.1 | 28.1 | 52.5 | 42.1 | 57.7 |
| Density, kg/m$^3$ | 0.84 | 0.84 | 0.72 | 616.1 | 438 | 438.1 | 467.4 | 477.4 | 467.7 |
| COMPONENTS, mol % | | | | | | | | | |
| Ethylene | 0.0 | 0.0 | 15.1 | 15.1 | 99.4 | 99.4 | 0.1 | 0.3 | 0.0 |
| Propylene | 0.0 | 0.0 | 28.7 | 28.7 | 0.6 | 0.6 | 33.7 | 99.5 | 0.5 |
| Propane | 0.0 | 0.0 | 0.0 | 0.0 | 0.0 | 0.0 | 0.0 | 0.0 | 0.0 |
| 1-Butene | 0.0 | 0.0 | 3.1 | 3.1 | 0.0 | 0.0 | 3.6 | 0.1 | 5.4 |
| Isobutene | 0.0 | 0.0 | 6.5 | 6.5 | 0.0 | 0.0 | 7.6 | 0.2 | 11.4 |
| cis-2-butene | 35.4 | 35.4 | 9.2 | 9.2 | 0.0 | 0.0 | 10.8 | 0.0 | 16.2 |
| trans-2-butene | 35.4 | 35.4 | 9.8 | 9.8 | 0.0 | 0.0 | 11.5 | 0.0 | 17.3 |
| n-Butane | 29.3 | 29.3 | 25.2 | 25.2 | 0.0 | 0.0 | 29.7 | 0.0 | 44.6 |
| 1-Pentene | 0.0 | 0.0 | 0.1 | 0.1 | 0.0 | 0.0 | 0.2 | 0.0 | 0.2 |
| cis-2-Pentene | 0.0 | 0.0 | 0.2 | 0.2 | 0.0 | 0.0 | 0.2 | 0.0 | 0.3 |
| trans-2-Pentene | 0.0 | 0.0 | 0.3 | 0.3 | 0.0 | 0.0 | 0.4 | 0.0 | 0.6 |
| 2-Methyl-2-butene | 0.0 | 0.0 | 0.8 | 0.8 | 0.0 | 0.0 | 1.0 | 0.0 | 1.5 |
| 3-Methyl-1-butene | 0.0 | 0.0 | 0.1 | 0.1 | 0.0 | 0.0 | 0.1 | 0.0 | 0.2 |
| 2-Methyl-1-butene | 0.0 | 0.0 | 0.5 | 0.5 | 0.0 | 0.0 | 0.5 | 0.0 | 0.8 |
| Sum of pentenes, pentanes, hexenes, hexanes, and heavier | 0.0 | 0.0 | 0.5 | 0.5 | 0.0 | 0.0 | 0.5 | 0.0 | 1.0 |
| Total mol % | 100 | 100 | 100 | 100 | 100 | 100 | 100 | 100 | 100 |

Example 4

The systems of FIG. 4 were also computer modeled using Aspen Plus®. The subsequent tables (Tables 13-16) depict the stream compositions as well as thermal properties for selected streams. The system inlet stream composition and catalyst reaction rates used for the model were the same as those of Example 1. The stream number corresponds with the stream or stream segment shown in FIG. 4. Simulations were run for 100% efficiency and 80% efficiency. Additionally, data is provided on a weight basis and a mole basis for each simulation. Table 13 depicts data for a simulation of the system of FIG. 4 with 100% efficiency and shows components on a mass basis. Table 14 depicts data for a simulation of the system of FIG. 4 with 100% efficiency and shows components on a mole basis. Table 15 depicts data for a simulation of the system of FIG. 4 with 80% efficiency and shows components on a mass basis. Table 16 depicts data for a simulation of the system of FIG. 4 with 80% efficiency and shows components on a mole basis. Additionally, FIG. 10 depicts a bar graph displaying the product distribution of the system of FIG. 4 as shown in Table 13 where, on the bar graph, "Propylene" corresponds with the stream of transfer line 507, "Ethylene" corresponds with the stream of transfer line 505, "Light Purge" corresponds with the stream of transfer line 504, "C4 Purge" corresponds with the stream of transfer line 516, and "C5+Heavy" corresponds with the stream of transfer line 514. The product distribution of FIG. 10 are based on the Aspen simulations of Table 13.

TABLE 13

FIG. 4 with 100% Efficiency in wt. %

| Stream Number | 501A | 501D | 510 | 503A | 503B | 504 | 505 | 506 | 507 | 508 | 512 | 516 | 514 |
|---|---|---|---|---|---|---|---|---|---|---|---|---|---|
| Mole Flow, kmol/hr | 100 | 100 | 120 | 528 | 528 | 27 | 3 | 499 | 52 | 446 | 402 | 37 | 8 |
| Mass Flow, kg/hr | 5670 | 5670 | 5670 | 29468 | 29468 | 741 | 82 | 28644 | 2202 | 26443 | 23799 | 2098 | 547 |
| Volume Flow m$^3$/hr | 6750 | 6750 | 8119 | 1310 | 47.9 | 1.7 | 0.2 | 62.3 | 4.6 | 56.1 | 57.4 | 4.2 | 1 |
| Enthalpy, MW | 0.6 | 0.6 | 1.1 | 0.6 | −10.3 | 0.2 | 0 | −8.8 | 0 | −8.9 | −8.3 | −0.8 | −0.2 |
| MW, g/mol | 56.7 | 56.7 | 47.2 | 55.8 | 55.8 | 27.8 | 27.9 | 57.5 | 42.1 | 59.3 | 59.3 | 57.4 | 67.4 |
| Density, kg/m$^3$ | 0.84 | 0.84 | 0.7 | 22.49 | 615.4 | 439.9 | 440 | 460 | 477.3 | 471 | 414.8 | 493.8 | 544.2 |
| COMPONENTS, wt. % | | | | | | | | | | | | | |
| Methane | 0.0 | 0.0 | 0.0 | 0.1 | 0.1 | 1.9 | 1.9 | 0.0 | 0.0 | 0.0 | 0.0 | 0.0 | 0.0 |
| Ethane | 0.0 | 0.0 | 0.0 | 0.0 | 0.0 | 0.2 | 0.2 | 0.0 | 0.3 | 0.0 | 0.0 | 0.0 | 0.0 |
| Ethylene | 0.0 | 0.0 | 18.2 | 5.5 | 5.5 | 97.8 | 97.8 | 0.0 | 0.3 | 0.0 | 0.0 | 0.0 | 0.0 |
| Propylene | 0.0 | 0.0 | 34.6 | 9.8 | 9.8 | 0.1 | 0.1 | 10.4 | 97.1 | 0.2 | 0.2 | 0.3 | 0.0 |
| Propane | 0.0 | 0.0 | 0.0 | 0.2 | 0.2 | 0.0 | 0.0 | 0.2 | 1.7 | 0.0 | 0.0 | 0.0 | 0.0 |
| 1-Butene | 0.0 | 0.0 | 3.7 | 1.1 | 1.1 | 0.0 | 0.0 | 1.1 | 0.0 | 1.3 | 1.3 | 1.5 | 0.3 |
| Isobutene | 0.0 | 0.0 | 7.8 | 20.0 | 20.0 | 0.0 | 0.0 | 21.2 | 0.6 | 23.7 | 23.7 | 27.9 | 4.5 |
| cis-2-butene | 35.4 | 35.4 | 3.7 | 0.9 | 0.9 | 0.0 | 0.0 | 1.0 | 0.0 | 1.1 | 1.1 | 1.0 | 1.5 |
| trans-2-butene | 35.4 | 35.4 | 4.5 | 1.1 | 1.1 | 0.0 | 0.0 | 1.2 | 0.0 | 1.4 | 1.4 | 1.4 | 1.2 |
| n-Butane | 29.3 | 29.3 | 24.3 | 56.4 | 56.4 | 0.0 | 0.0 | 59.8 | 0.0 | 66.8 | 66.8 | 67.8 | 61.8 |
| 1-Pentene | 0.0 | 0.0 | 0.2 | 0.1 | 0.1 | 0.0 | 0.0 | 0.1 | 0.0 | 0.2 | 0.2 | 0.0 | 0.8 |
| cis-2-Pentene | 0.0 | 0.0 | 0.2 | 0.1 | 0.1 | 0.0 | 0.0 | 0.1 | 0.0 | 0.1 | 0.1 | 0.0 | 0.3 |
| trans-2-Pentene | 0.0 | 0.0 | 0.4 | 0.1 | 0.1 | 0.0 | 0.0 | 0.1 | 0.0 | 0.1 | 0.1 | 0.0 | 0.7 |
| 2-Methyl-2-butene | 0.0 | 0.0 | 1.0 | 0.2 | 0.2 | 0.0 | 0.0 | 0.3 | 0.0 | 0.3 | 0.3 | 0.0 | 1.6 |
| 3-Methyl-1-butene | 0.0 | 0.0 | 0.1 | 0.0 | 0.0 | 0.0 | 0.0 | 0.0 | 0.0 | 0.1 | 0.1 | 0.0 | 0.2 |
| 2-Methyl-1-butene | 0.0 | 0.0 | 0.6 | 0.1 | 0.1 | 0.0 | 0.0 | 0.1 | 0.0 | 0.2 | 0.2 | 0.0 | 0.8 |
| 2-Methy-butane | 0.0 | 0.0 | 0.0 | 0.1 | 0.1 | 0.0 | 0.0 | 0.1 | 0.0 | 0.1 | 0.1 | 0.0 | 0.3 |
| n-Pentane | 0.0 | 0.0 | 0.0 | 0.1 | 0.1 | 0.0 | 0.0 | 0.1 | 0.0 | 0.1 | 0.1 | 0.0 | 0.4 |
| Sum of pentenes, pentanes, hexenes, hexanes, and heavier | 0.0 | 0.0 | 0.6 | 3.9 | 3.9 | 0.0 | 0.0 | 4.3 | 0.0 | 4.6 | 4.6 | 0.0 | 25.5 |
| Total wt. % | 100 | 100 | 100 | 100 | 100 | 100 | 100 | 100 | 100 | 100 | 100 | 100 | 100 |

TABLE 14

FIG. 4 with 100% Efficiency in mol %

| Stream Number | 501A | 501D | 510 | 503A | 503B | 504 | 505 | 506 | 507 | 508 | 512 | 516 | 514 |
|---|---|---|---|---|---|---|---|---|---|---|---|---|---|
| Mole Flow, kmol/hr | 100 | 100 | 120 | 528 | 528 | 27 | 3 | 499 | 52 | 446 | 402 | 37 | 8 |
| Mass Flow, kg/hr | 5670 | 5670 | 5670 | 29468 | 29468 | 741 | 82 | 28644 | 2202 | 26443 | 23799 | 2098 | 547 |
| Volume Flow m$^3$/hr | 6750 | 6750 | 8119 | 1310 | 47.9 | 1.7 | 0.2 | 62.3 | 4.6 | 56.1 | 57.4 | 4.2 | 1 |
| Enthalpy, MW | 0.6 | 0.6 | 1.1 | 0.6 | −10.3 | 0.2 | 0 | −8.8 | 0 | −8.9 | −8.3 | −0.8 | −0.2 |
| MW, g/mol | 56.7 | 56.7 | 47.2 | 55.8 | 55.8 | 27.8 | 27.9 | 57.5 | 42.1 | 59.3 | 59.3 | 57.4 | 67.4 |
| Density, kg/m$^3$ | 0.84 | 0.84 | 0.7 | 22.49 | 615.4 | 439.9 | 440 | 460 | 477.3 | 471 | 414.8 | 493.8 | 544.2 |
| COMPONENTS, mol % | | | | | | | | | | | | | |
| Methane | 0.0 | 0.0 | 0.0 | 0.1 | 0.1 | 1.9 | 1.9 | 0.0 | 0.0 | 0.0 | 0.0 | 0.0 | 0.0 |
| Ethane | 0.0 | 0.0 | 0.0 | 0.0 | 0.0 | 0.2 | 0.2 | 0.0 | 0.3 | 0.0 | 0.0 | 0.0 | 0.0 |
| Ethylene | 0.0 | 0.0 | 18.2 | 5.5 | 5.5 | 97.8 | 97.8 | 0.0 | 0.3 | 0.0 | 0.0 | 0.0 | 0.0 |
| Propylene | 0.0 | 0.0 | 34.6 | 9.8 | 9.8 | 0.1 | 0.1 | 10.4 | 97.1 | 0.2 | 0.2 | 0.3 | 0.0 |
| Propane | 0.0 | 0.0 | 0.0 | 0.2 | 0.2 | 0.0 | 0.0 | 0.2 | 1.7 | 0.0 | 0.0 | 0.0 | 0.0 |
| 1-Butene | 0.0 | 0.0 | 3.7 | 1.1 | 1.1 | 0.0 | 0.0 | 1.1 | 0.0 | 1.3 | 1.3 | 1.5 | 0.3 |
| Isobutene | 0.0 | 0.0 | 7.8 | 20.0 | 20.0 | 0.0 | 0.0 | 21.2 | 0.6 | 23.7 | 23.7 | 27.9 | 4.5 |
| cis-2-butene | 35.4 | 35.4 | 3.7 | 0.9 | 0.9 | 0.0 | 0.0 | 1.0 | 0.0 | 1.1 | 1.1 | 1.0 | 1.5 |
| trans-2-butene | 35.4 | 35.4 | 4.5 | 1.1 | 1.1 | 0.0 | 0.0 | 1.2 | 0.0 | 1.4 | 1.4 | 1.4 | 1.2 |
| n-Butane | 29.3 | 29.3 | 24.3 | 56.4 | 56.4 | 0.0 | 0.0 | 59.8 | 0.0 | 66.8 | 66.8 | 67.8 | 61.8 |
| 1-Pentene | 0.0 | 0.0 | 0.2 | 0.1 | 0.1 | 0.0 | 0.0 | 0.1 | 0.0 | 0.2 | 0.2 | 0.0 | 0.8 |
| cis-2-Pentene | 0.0 | 0.0 | 0.2 | 0.1 | 0.1 | 0.0 | 0.0 | 0.1 | 0.0 | 0.1 | 0.1 | 0.0 | 0.3 |
| trans-2-Pentene | 0.0 | 0.0 | 0.4 | 0.1 | 0.1 | 0.0 | 0.0 | 0.1 | 0.0 | 0.1 | 0.1 | 0.0 | 0.7 |
| 2-Methyl-2-butene | 0.0 | 0.0 | 1.0 | 0.2 | 0.2 | 0.0 | 0.0 | 0.3 | 0.0 | 0.3 | 0.3 | 0.0 | 1.6 |

TABLE 14-continued

FIG. 4 with 100% Efficiency in mol %

| Stream Number | 501A | 501D | 510 | 503A | 503B | 504 | 505 | 506 | 507 | 508 | 512 | 516 | 514 |
|---|---|---|---|---|---|---|---|---|---|---|---|---|---|
| 3-Methyl-1-butene | 0.0 | 0.0 | 0.1 | 0.0 | 0.0 | 0.0 | 0.0 | 0.0 | 0.0 | 0.1 | 0.1 | 0.0 | 0.2 |
| 2-Methyl-1-butene | 0.0 | 0.0 | 0.6 | 0.1 | 0.1 | 0.0 | 0.0 | 0.1 | 0.0 | 0.2 | 0.2 | 0.0 | 0.8 |
| 2-Methy-butane | 0.0 | 0.0 | 0.0 | 0.1 | 0.1 | 0.0 | 0.0 | 0.1 | 0.0 | 0.1 | 0.1 | 0.0 | 0.3 |
| n-Pentane | 0.0 | 0.0 | 0.0 | 0.1 | 0.1 | 0.0 | 0.0 | 0.1 | 0.0 | 0.1 | 0.1 | 0.0 | 0.4 |
| Sum of pentenes, | 0.0 | 0.0 | 0.6 | 3.9 | 3.9 | 0.0 | 0.0 | 4.3 | 0.0 | 4.6 | 4.6 | 0.0 | 25.5 |
| pentanes, hexenes, hexanes, and heavier | | | | | | | | | | | | | |
| Total mol % | 100 | 100 | 100 | 100 | 100 | 100 | 100 | 100 | 100 | 100 | 100 | 100 | 100 |

TABLE 15

FIG. 4 with 80% Efficiency in wt. %

| Stream Number | 501A | 501D | 510 | 503A | 503B | 504 | 505 | 506 | 507 | 508 | 512 | 516 | 514 |
|---|---|---|---|---|---|---|---|---|---|---|---|---|---|
| Mole Flow, kmol/hr | 100 | 100 | 116 | 540 | 540 | 27 | 3 | 511 | 50 | 461 | 415 | 39 | 7 |
| Mass Flow, kg/hr | 5670 | 5670 | 5670 | 30436 | 30436 | 739 | 82 | 29616 | 2096 | 27519 | 24767 | 2218 | 534 |
| Volume Flow m$^3$/hr | 6750 | 6750 | 7845 | 1220 | 49 | 1.7 | 0.2 | 63.7 | 4.4 | 57.8 | 63.1 | 4.5 | 0.9 |
| Enthalpy, MW | 0.6 | 0.6 | 1 | −0.6 | −10.4 | 0.2 | 0 | −8.8 | 0 | −8.9 | −8.3 | −0.8 | −0.1 |
| MW, g/mol | 56.7 | 56.7 | 48.8 | 56.3 | 56.3 | 27.7 | 27.7 | 58 | 42.1 | 59.7 | 59.7 | 57.5 | 71.3 |
| Density, kg/m$^3$ | 0.84 | 0.84 | 0.72 | 24.94 | 620.7 | 441.4 | 441.4 | 464.8 | 476.9 | 476.3 | 392.4 | 493.9 | 572.6 |
| COMPONENTS, wt. % | | | | | | | | | | | | | |
| Methane | 0.0 | 0.0 | 0.0 | 0.0 | 0.0 | 1.8 | 1.8 | 0.0 | 0.0 | 0.0 | 0.0 | 0.0 | 0.0 |
| Ethane | 0.0 | 0.0 | 0.0 | 0.0 | 0.0 | 0.2 | 0.2 | 0.0 | 0.4 | 0.0 | 0.0 | 0.0 | 0.0 |
| Ethylene | 0.0 | 0.0 | 8.7 | 2.7 | 2.7 | 98.0 | 98.0 | 0.0 | 0.2 | 0.0 | 0.0 | 0.0 | 0.0 |
| Propylene | 0.0 | 0.0 | 24.7 | 6.7 | 6.7 | 0.0 | 0.0 | 6.8 | 95.9 | 0.1 | 0.1 | 0.1 | 0.0 |
| Propane | 0.0 | 0.0 | 0.0 | 0.2 | 0.2 | 0.0 | 0.0 | 0.2 | 3.1 | 0.0 | 0.0 | 0.0 | 0.0 |
| 1-Butene | 0.0 | 0.0 | 3.5 | 1.1 | 1.1 | 0.0 | 0.0 | 1.1 | 0.0 | 1.2 | 1.2 | 1.4 | 0.0 |
| Isobutene | 0.0 | 0.0 | 7.4 | 17.7 | 17.7 | 0.0 | 0.0 | 18.1 | 0.3 | 19.5 | 19.5 | 23.7 | 1.9 |
| cis-2-butene | 35.0 | 35.0 | 10.5 | 2.5 | 2.5 | 0.0 | 0.0 | 2.6 | 0.0 | 2.7 | 2.7 | 2.7 | 2.9 |
| trans-2-butene | 35.0 | 35.0 | 11.3 | 2.7 | 2.7 | 0.0 | 0.0 | 2.7 | 0.0 | 2.9 | 2.9 | 3.2 | 1.9 |
| n-Butane | 30.0 | 30.0 | 30.0 | 57.3 | 57.3 | 0.0 | 0.0 | 58.8 | 0.1 | 63.3 | 63.3 | 68.7 | 40.8 |
| 1-Pentene | 0.0 | 0.0 | 0.2 | 0.3 | 0.3 | 0.0 | 0.0 | 0.3 | 0.0 | 0.3 | 0.3 | 0.0 | 1.4 |
| cis-2-Pentene | 0.0 | 0.0 | 0.3 | 0.1 | 0.1 | 0.0 | 0.0 | 0.1 | 0.0 | 0.1 | 0.1 | 0.0 | 0.3 |
| trans-2-Pentene | 0.0 | 0.0 | 0.5 | 0.1 | 0.1 | 0.0 | 0.0 | 0.1 | 0.0 | 0.1 | 0.1 | 0.0 | 0.6 |
| 2-Methyl-2-butene | 0.0 | 0.0 | 1.2 | 0.3 | 0.3 | 0.0 | 0.0 | 0.3 | 0.0 | 0.3 | 0.3 | 0.0 | 1.6 |
| 3-Methyl-1-butene | 0.0 | 0.0 | 0.2 | 0.1 | 0.1 | 0.0 | 0.0 | 0.1 | 0.0 | 0.1 | 0.1 | 0.0 | 0.2 |
| 2-Methyl-1-butene | 0.0 | 0.0 | 0.7 | 0.2 | 0.2 | 0.0 | 0.0 | 0.2 | 0.0 | 0.2 | 0.2 | 0.0 | 0.9 |
| 2-Methy-butane | 0.0 | 0.0 | 0.0 | 0.1 | 0.1 | 0.0 | 0.0 | 0.1 | 0.0 | 0.1 | 0.1 | 0.0 | 0.3 |
| n-Pentane | 0.0 | 0.0 | 0.0 | 0.1 | 0.1 | 0.0 | 0.0 | 0.1 | 0.0 | 0.1 | 0.1 | 0.0 | 0.4 |
| Sum of pentenes, | 0.0 | 0.0 | 1.0 | 8.1 | 8.1 | 0.0 | 0.0 | 8.3 | 0.0 | 8.9 | 8.9 | 0.0 | 46.5 |
| pentanes, hexenes, hexanes, and heavier | | | | | | | | | | | | | |
| Total wt. % | 100 | 100 | 100 | 100 | 100 | 100 | 100 | 100 | 100 | 100 | 100 | 100 | 100 |

TABLE 16

FIG. 4 with 80% Efficiency in mol %

| Stream Number | 501A | 501D | 510 | 503A | 503B | 504 | 505 | 506 | 507 | 508 | 512 | 516 | 514 |
|---|---|---|---|---|---|---|---|---|---|---|---|---|---|
| Mole Flow, kmol/hr | 100 | 100 | 116 | 540 | 540 | 27 | 3 | 511 | 50 | 461 | 415 | 39 | 7 |
| Mass Flow, kg/hr | 5670 | 5670 | 5670 | 30436 | 30436 | 739 | 82 | 29616 | 2096 | 27519 | 24767 | 2218 | 534 |
| Volume Flow m$^3$/hr | 6750 | 6750 | 7845 | 1220 | 49 | 1.7 | 0.2 | 63.7 | 4.4 | 57.8 | 63.1 | 4.5 | 0.9 |
| Enthalpy, MW | 0.6 | 0.6 | 1 | −0.6 | −10.4 | 0.2 | 0 | −8.8 | 0 | −8.9 | −8.3 | −0.8 | −0.1 |
| MW, g/mol | 56.7 | 56.7 | 48.8 | 56.3 | 56.3 | 27.7 | 27.7 | 58 | 42.1 | 59.7 | 59.7 | 57.5 | 71.3 |
| Density, kg/m$^3$ | 0.84 | 0.84 | 0.72 | 24.94 | 620.7 | 441.4 | 441.4 | 464.8 | 476.9 | 476.3 | 392.4 | 493.9 | 572.6 |
| COMPONENTS, mol % | | | | | | | | | | | | | |
| Methane | 0.0 | 0.0 | 0.0 | 0.2 | 0.2 | 3.1 | 3.1 | 0.0 | 0.0 | 0.0 | 0.0 | 0.0 | 0.0 |
| Ethane | 0.0 | 0.0 | 0.0 | 0.1 | 0.1 | 0.2 | 0.2 | 0.1 | 0.6 | 0.0 | 0.0 | 0.0 | 0.0 |
| Ethylene | 0.0 | 0.0 | 15.1 | 5.3 | 5.3 | 96.7 | 96.7 | 0.0 | 0.3 | 0.0 | 0.0 | 0.0 | 0.0 |
| Propylene | 0.0 | 0.0 | 28.7 | 8.9 | 8.9 | 0.0 | 0.0 | 9.4 | 95.9 | 0.1 | 0.1 | 0.1 | 0.0 |
| Propane | 0.0 | 0.0 | 0.0 | 0.3 | 0.3 | 0.0 | 0.0 | 0.3 | 2.9 | 0.0 | 0.0 | 0.0 | 0.0 |

TABLE 16-continued

FIG. 4 with 80% Efficiency in mol %

| Stream Number | 501A | 501D | 510 | 503A | 503B | 504 | 505 | 506 | 507 | 508 | 512 | 516 | 514 |
|---|---|---|---|---|---|---|---|---|---|---|---|---|---|
| 1-Butene | 0.0 | 0.0 | 3.1 | 1.1 | 1.1 | 0.0 | 0.0 | 1.1 | 0.0 | 1.3 | 1.3 | 1.5 | 0.2 |
| Isobutene | 0.0 | 0.0 | 6.5 | 17.7 | 17.7 | 0.0 | 0.0 | 18.8 | 0.2 | 20.8 | 20.8 | 24.3 | 2.4 |
| cis-2-butene | 35.4 | 35.4 | 9.2 | 2.5 | 2.5 | 0.0 | 0.0 | 2.6 | 0.0 | 2.9 | 2.9 | 2.8 | 3.7 |
| trans-2-butene | 35.4 | 35.4 | 9.8 | 2.7 | 2.7 | 0.0 | 0.0 | 2.8 | 0.0 | 3.1 | 3.1 | 3.3 | 2.4 |
| n-Butane | 29.3 | 29.3 | 25.2 | 55.5 | 55.5 | 0.0 | 0.0 | 58.7 | 0.1 | 65.1 | 65.1 | 68.0 | 50.1 |
| 1-Pentene | 0.0 | 0.0 | 0.1 | 0.2 | 0.2 | 0.0 | 0.0 | 0.2 | 0.0 | 0.3 | 0.3 | 0.0 | 1.4 |
| cis-2-Pentene | 0.0 | 0.0 | 0.2 | 0.0 | 0.0 | 0.0 | 0.0 | 0.0 | 0.0 | 0.1 | 0.1 | 0.0 | 0.3 |
| trans-2-Pentene | 0.0 | 0.0 | 0.3 | 0.1 | 0.1 | 0.0 | 0.0 | 0.1 | 0.0 | 0.1 | 0.1 | 0.0 | 0.7 |
| 2-Methyl-2-butene | 0.0 | 0.0 | 0.8 | 0.2 | 0.2 | 0.0 | 0.0 | 0.2 | 0.0 | 0.3 | 0.3 | 0.0 | 1.6 |
| 3-Methyl-1-butene | 0.0 | 0.0 | 0.1 | 0.0 | 0.0 | 0.0 | 0.0 | 0.1 | 0.0 | 0.1 | 0.1 | 0.0 | 0.3 |
| 2-Methyl-1-butene | 0.0 | 0.0 | 0.5 | 0.1 | 0.1 | 0.0 | 0.0 | 0.1 | 0.0 | 0.1 | 0.1 | 0.0 | 0.9 |
| 2-Methy-butane | 0.0 | 0.0 | 0.0 | 0.1 | 0.1 | 0.0 | 0.0 | 0.1 | 0.0 | 0.1 | 0.1 | 0.0 | 0.3 |
| n-Pentane | 0.0 | 0.0 | 0.0 | 0.1 | 0.1 | 0.0 | 0.0 | 0.1 | 0.0 | 0.1 | 0.1 | 0.0 | 0.4 |
| Sum of pentenes, pentanes, hexenes, hexanes, and heavier | 0.0 | 0.0 | 0.5 | 4.7 | 4.7 | 0.0 | 0.0 | 5.2 | 0.0 | 5.8 | 5.8 | 0.0 | 35.4 |
| Total mol % | 100 | 100 | 100 | 100 | 100 | 100 | 100 | 100 | 100 | 100 | 100 | 100 | 100 |

Example 5

Table 17 shows butene conversion, propylene selectivity, and propylene yield for the embodiments of FIGS. 1-4. The data was determined using Aspen Plus® with the conditions as those provided for Tables 1, 5, 9, and 13.

The butene conversion is defined as:

$$\left(1 - \frac{\text{Mass flow of 2-butene in combined reactor effluent}}{\text{Mass flow of 2-butene in combined reactor feed}}\right) * 100$$

The propylene selectivity is defined as:

$$\left(\frac{\text{Mass flow of propylene in reactor effluent} - \text{Mass flow of propylene in reactor feed}}{\text{Mass flow of 2-butene in reactor feed} * \text{butene conversion rate}}\right) * 100\%$$

The propylene yield is defined as:

$$\left(\frac{\text{Total Propylene Produced (wt. \%)}}{\text{Total butene 2 in Feed (wt. \%)}}\right) * 100\%$$

TABLE 17

| | Embodiment of FIG. 1 | Embodiment of FIG. 2 | Embodiment of FIG. 3 | Embodiment of FIG. 4 |
|---|---|---|---|---|
| Butene Conversion | 86.1% | 83.0% | 86.1% | 86.3% |
| Propylene selectivity | 51.3% | 64.3% | 51.3% | 54.8% |
| Propylene yield | 44.1% | 61.8% | 44.1% | 54.0% |

For the purposes of describing and defining the present disclosure it is noted that the term "about" are utilized in this disclosure to represent the inherent degree of uncertainty that may be attributed to any quantitative comparison, value, measurement, or other representation. The term "about" are also utilized in this disclosure to represent the degree by which a quantitative representation may vary from a stated reference without resulting in a change in the basic function of the subject matter at issue. Additionally, the term "consisting essentially of" is used in this disclosure to refer to quantitative values that do not materially affect the basic and novel characteristic(s) of the disclosure. For example, a chemical stream "consisting essentially" of a particular chemical constituent or group of chemical constituents should be understood to mean that the stream includes at least about 99.5% of a that particular chemical constituent or group of chemical constituents.

It should be appreciated that compositional ranges of a chemical constituent in a stream or in a reactor should be appreciated as containing, in some embodiments, a mixture of isomers of that constituent. For example, a compositional range specifying butene may include a mixture of various isomers of butene. It should be appreciated that the examples supply compositional ranges for various streams, and that the total amount of isomers of a particular chemical composition can constitute a range.

It is noted that one or more of the following claims utilize the term "where" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that any two quantitative values assigned to a property may constitute a range of that property, and all combinations of ranges formed from all stated quantitative values of a given property are contemplated in this disclosure.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the claims appended hereto should be taken as the sole representation of the breadth of the present disclosure and the corresponding scope of the various embodiments described in this disclosure. Further, it will be apparent that modifications and variations are possible without departing from the scope of the appended claims.

What is claimed is:

1. A process for producing propylene, the process comprising:
introducing a first stream comprising butene to a reactor, where the reactor comprises a metathesis catalyst and a cracking catalyst, the metathesis catalyst positioned generally upstream of the cracking catalyst;
at least partially metathesizing the first stream with the metathesis catalyst to form a metathesis-reaction product;
at least partially cracking the metathesis-reaction product with the cracking catalyst to form a cracking-reaction product comprising butene;
passing the cracking-reaction product out of the reactor in a cracking-reaction product stream; and
at least partially separating propylene from the cracking-reaction product stream to form a product stream comprising propylene,
where:
at least a portion of the butene in the cracking-reaction product stream is recycled by at least partially separating butene in the cracking-reaction product stream to form a recycle stream comprising butene; and
the first stream is a mixture of the recycle stream and a system inlet stream.

2. The process of claim 1, where the first stream comprises at least 20 wt. % butene.

3. The process of claim 1, where the system inlet stream comprises at least 50 wt. % butene.

4. The process of claim 1, where the recycle stream comprises at least 80 wt. % of butane and butene.

5. The process of claim 1, where the cracking-reaction product comprises at least 4 wt. % propylene.

6. The process of claim 1, where the product stream comprises at least 90 wt. % propylene.

7. The process of claim 1, where:
the metathesis catalyst comprises a mesoporous silica catalyst impregnated with metal oxide, where the mesoporous silica catalyst includes a pore size distribution of about 2.5 nm to about 40 nm and a total pore volume of at least about 0.600 cm$^3$/g; and
the cracking catalyst comprises a mordenite framework inverted (MFI) structured silica catalyst downstream of the mesoporous silica catalyst, where the MFI structured silica catalyst includes total acidity of 0.001 mmol/g to 0.1 mmol/g.

8. The process of claim 1, where the metathesis catalyst comprises an amorphous mesoporous silica foam impregnated with metal oxides, where the metathesis catalyst has a pore size distribution of at least 3 nm to 40 nm and a total pore volume of at least 0.700 cm$^3$/g.

9. A process for producing propylene, the process comprising:
introducing a first stream comprising butene to a first reactor, the first reactor comprising a metathesis catalyst;
at least partially metathesizing the first stream in the first reactor to form a metathesis-reaction product;
passing the metathesis-reaction product out of the first reactor in a metathesis-reaction product stream to a second reactor, the second reactor comprising a cracking catalyst;
at least partially cracking the metathesis-reaction product stream in the second reactor to form a cracking-reaction product;
passing the cracking-reaction product out of the second reactor in a cracking-reaction product stream comprising butene; and
at least partially separating propylene from the cracking-reaction product stream to form a product stream comprising propylene,
where:
at least a portion of the butene in the cracking-reaction product stream is recycled by at least partially separating butene from the cracking-reaction product stream to form a recycle stream comprising butene; and
the recycle stream is mixed with the metathesis-reaction product stream.

10. The process of claim 9, where the first stream is a system inlet stream comprising at least 50 wt. % butene.

11. The process of claim 9, where the cracking-reaction product comprises at least 4 wt. % propylene.

12. The process of claim 9, where the product stream comprises at least 90 wt. % propylene.

13. The process of claim 9, where the recycle stream comprises at least 90 wt. % of butane and butene.

14. The process of claim 9, where:
the metathesis catalyst comprises a mesoporous silica catalyst impregnated with metal oxide, where the mesoporous silica catalyst includes a pore size distribution of about 2.5 nm to about 40 nm and a total pore volume of at least about 0.600 cm$^3$/g; and
the cracking catalyst comprises a mordenite framework inverted (MFI) structured silica catalyst downstream of the mesoporous silica catalyst, where the MFI structured silica catalyst includes total acidity of 0.001 mmol/g to 0.1 mmol/g.

15. The process of claim 9, where the metathesis catalyst comprises an amorphous mesoporous silica foam impregnated with metal oxides, where the metathesis catalyst has a pore size distribution of at least 3 nm to 40 nm and a total pore volume of at least 0.700 cm$^3$/g.

* * * * *